United States Patent
Takahashi et al.

(10) Patent No.: US 11,113,810 B2
(45) Date of Patent: Sep. 7, 2021

(54) X-RAY CT SCANNER, IMAGE GENERATION METHOD, AND IMAGE GENERATION PROGRAM

(71) Applicant: Hitachi, Ltd., Tokyo (JP)

(72) Inventors: Hisashi Takahashi, Tokyo (JP); Taiga Gotou, Tokyo (JP); Koichi Hirokawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 7 days.

(21) Appl. No.: 16/628,254

(22) PCT Filed: Apr. 9, 2018

(86) PCT No.: PCT/JP2018/014957
§ 371 (c)(1),
(2) Date: Jan. 2, 2020

(87) PCT Pub. No.: WO2019/021543
PCT Pub. Date: Jan. 31, 2019

(65) Prior Publication Data
US 2020/0219251 A1      Jul. 9, 2020

(30) Foreign Application Priority Data
Jul. 27, 2017   (JP) .............................. JP2017-145779

(51) Int. Cl.
*G06K 9/00* (2006.01)
*G06T 7/00* (2017.01)
(Continued)

(52) U.S. Cl.
CPC ............ *G06T 7/0012* (2013.01); *G06T 5/002* (2013.01); *G06T 5/003* (2013.01); *G06T 17/10* (2013.01); *G06T 2207/10081* (2013.01)

(58) Field of Classification Search
CPC ....... G06T 7/0012; G06T 7/0014; G06T 7/13; G06T 7/12; G06T 7/162; G06T 7/337;
(Continued)

(56) References Cited

U.S. PATENT DOCUMENTS

2001/0028696 A1   10/2001   Yamada
2005/0254721 A1   11/2005   Hagiwara
(Continued)

FOREIGN PATENT DOCUMENTS

JP      2001-286463 A      10/2001
JP      2005-323926 A      11/2005
(Continued)

OTHER PUBLICATIONS

J. Hsieh, "Adaptive streak artifact reduction in computed tomography resulting from excessive x-ray photon noise", Med. Phys., vol. 25, No. 11, 1998, p. 2139-2147.
(Continued)

*Primary Examiner* — Jose L Couso
(74) *Attorney, Agent, or Firm* — Foley & Lardner LLP

(57) ABSTRACT

An image is generated where an edge of a structure in a subject is sharpened with reducing streak artifacts, within a short amount of time. X-rays at multiple angles are applied to the subject placed in imaging space, and a distribution of X-rays strength passing through the subject is detected to obtain raw data associated with multiple views. After smoothing the raw data associated with multiple views, image reconstruction is performed to generate a smoothed image of a predetermined region to be imaged in the imaging space. In the smoothed image, more intense sharpening process is applied to pixels in a region of a central part of the subject, than the pixels in a region of a peripheral part of the subject.

12 Claims, 14 Drawing Sheets

(51) Int. Cl.
*G06T 5/00* (2006.01)
*G06T 17/10* (2006.01)

(58) Field of Classification Search
CPC ....... G06T 7/0002; G06T 5/002; G06T 5/003; G06T 5/005; G06T 5/50; G06T 5/008; G06T 5/20; G06T 17/10; G06T 11/006; G06T 11/005; G06T 11/008; G06T 2207/10081; G06T 2207/30004; G06T 2207/20224; G06T 2207/10124; G06T 2207/30101; G06T 2207/30116; G06T 2207/10116; G06T 2207/20192; G06T 2207/20221; G06T 2207/30204; G06T 2207/20028; G06T 2207/20182; G06T 2211/412; G06T 2211/424; G06T 2211/421; G06T 2211/40; G06T 2211/408; G06T 2211/428; G06T 2210/41; A61B 6/03; A61B 6/032; A61B 6/5258; A61B 6/583; A61B 6/5205; A61B 6/027; A61B 6/025; A61B 6/4085; A61B 6/482; A61B 6/5252; A61B 6/584; A61B 6/484; A61B 6/4441; A61B 2090/3966; A61B 90/39; Y10S 378/901; G01N 2223/419; G01N 2223/42; G01N 23/046; G06K 9/36; G06K 9/40; G06K 9/44; H04N 5/32

See application file for complete search history.

(56) References Cited

U.S. PATENT DOCUMENTS

2006/0262895 A1* 11/2006 Kawachi .............. G01N 23/046
                                                    378/4
2010/0135563 A1* 6/2010 Kelly .................... G06T 7/0004
                                                    382/131
2015/0010224 A1 1/2015 Takahashi

FOREIGN PATENT DOCUMENTS

JP          2009-119289 A     6/2009
JP     WO-2013/146283 A1     10/2013

OTHER PUBLICATIONS

T. Li et. al., "Nonlinear Sinogram Smoothing for Low-Dose X-Ray CT", IEEE. Transactions on Nuclear Science, vol. 51, No. 5, 2004, pp. 2505-2513.

International Search Report with English translation and Written Opinion issued in corresponding application No. PCT/JP2018/014957 dated Jul. 3, 2018.

International Preliminary Report on Patentability issued in corresponding International Application No. PCT/JP2018/014957 dated Feb. 6, 2020, six (6) pages.

* cited by examiner

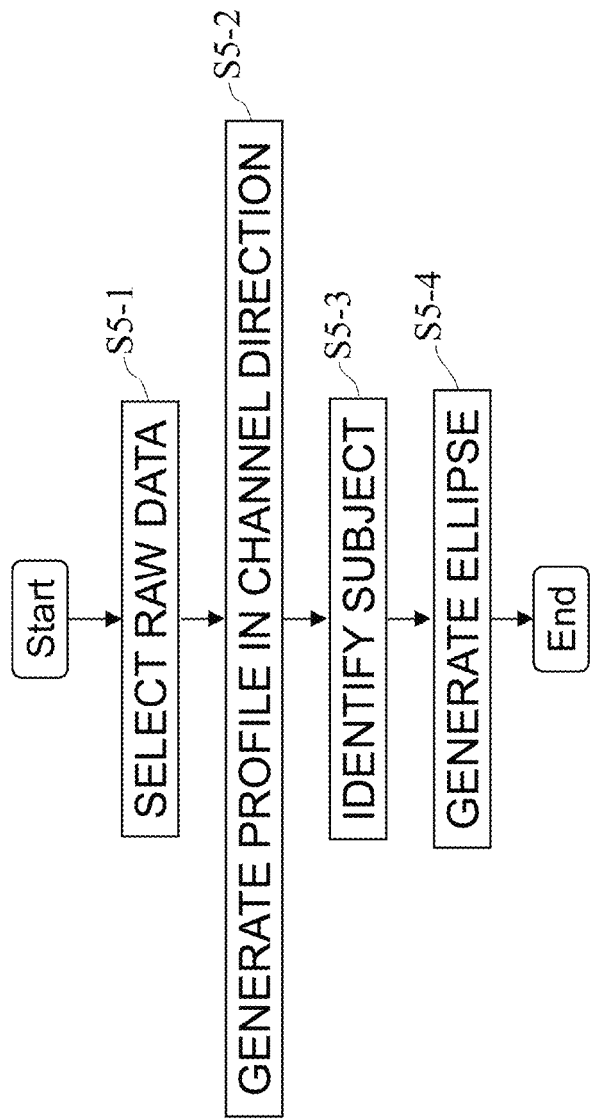

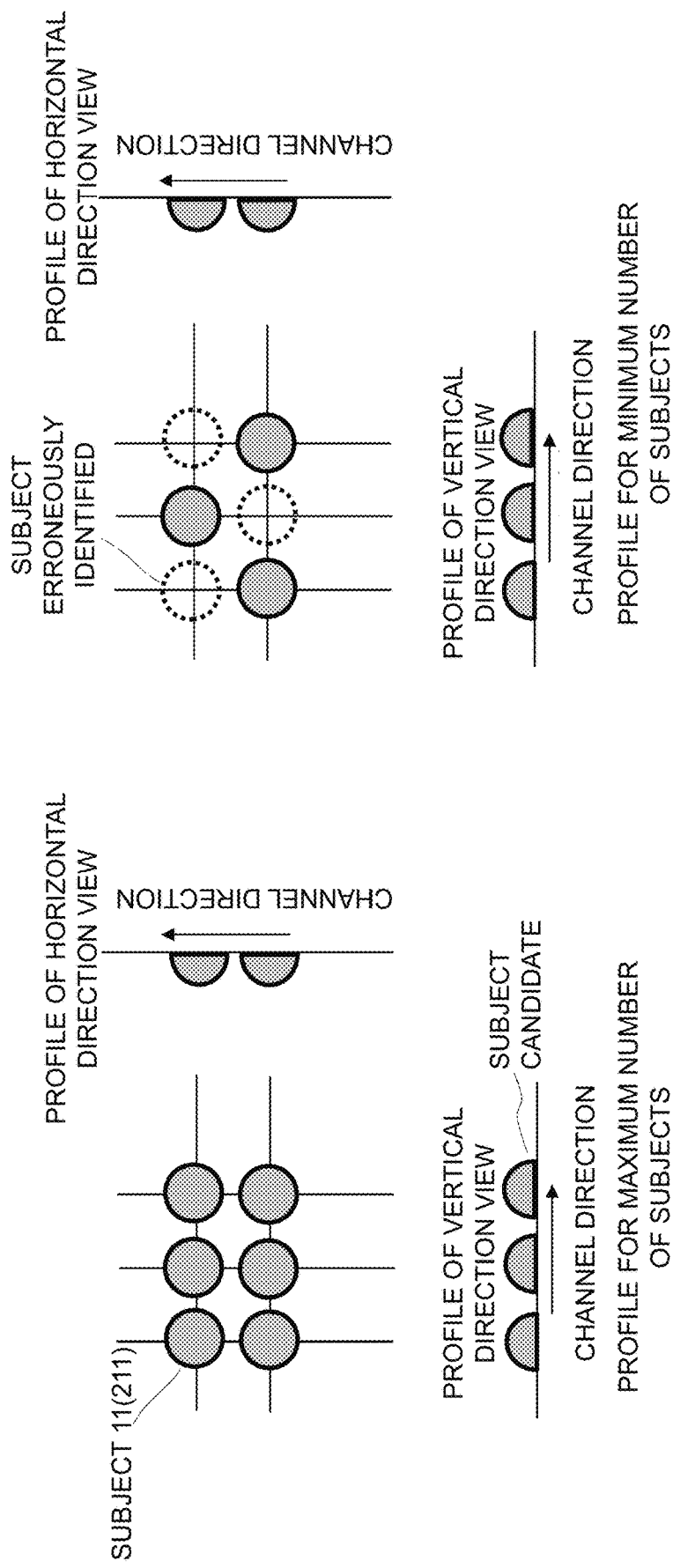

RAW-DATA FILTERING PROCESS APPLIED IMAGE

NORMAL RECONSTRUCTED IMAGE

X-RAY CT SCANNER, IMAGE GENERATION METHOD, AND IMAGE GENERATION PROGRAM

TECHNICAL FIELD

The present invention relates to an X-ray CT system, and more particularly, to an X-ray CT system that achieves both reduction of streak artifacts and edge sharpening of a structure in a generated CT image.

BACKGROUND ART

X-ray CT systems are widely used as medical-use tomographic imaging devices to create an image of a human body non-invasively. To address growing concern about radiation exposure in recent years, reduction of exposure dose is being demanded in CT scanning. However, if radiation dose of X-rays is insufficient in imaging a flat region such as shoulders, detected signals are likely to attenuate, resulting in increase of noise ratio, in a longitudinal direction where length of X-rays passing through a subject is long and a degree of X-ray attenuation is high. It is well known that this may cause streak artifacts in an image (FIG. 14A).

Given these circumstances, image processing methods have been extensively studied for improving an image quality when imaging is performed with low-dose radiation. By way of example, according to the documents such as Non Patent Literature 1 and Non Patent Literature 2, there is suggested a method for reducing impact of noise by applying a filter for smoothing detected signals (raw data) in response to strength of detected signals, thereby achieving reduction of streak artifacts.

However, when the smoothing filter is applied to the raw data, abrupt change in detected signal values is also smoothed on an edge part of the raw data associated with a relatively high-contrast structure in the subject. Accordingly, this may cause a problem that blurring is likely to occur at the edge of the high-contrast structure within the subject in a reconstructed image. There is a tradeoff between an effect of reducing streak artifacts and an effect of keeping sharpness on the edge of the structure, and thus when the former is enhanced, the latter becomes less effective. In other words, increasing the degree of smoothing of the raw data to reduce strong streak artifacts may cause higher blurring at the edge of the structure within the subject in the reconstructed image (FIG. 14B). Blurring at the edge of the structure within the subject is undesirable when the image is used for clinical diagnosis. Therefore, there is demanded a processing method for obtaining an image where streak artifacts are reduced with preventing the blurring at the edge of the structure in the subject.

As a solution of this problem, there is suggested in Patent Literature 1, a method of weighted addition that is performed adequately in adding an image (original image) reconstructed from raw data as it is, to an image (smoothed image) reconstructed from the raw data to which a smoothing filter has been applied. In this method, the weighted addition is performed in a manner that increases the ratio of smoothed-image pixel values in the pixels of a region where streak artifacts are generated on the image, to the original-image pixel values, whereas at the edge part of the structure within the subject, the ratio of the original-image pixel values increases to the smoothed-image pixel values. According to this method, a third image can be obtained where streak artifacts are reduced while blurring at the edge of the structure within the subject is prevented.

PRIOR ART DOCUMENTS

Non Patent Literatures

Non Patent Literature 1
J. Hsieh., "Adaptive streak artifact reduction in computed tomography resulting from excessive x-ray photon noise" Med. Phys., Vol. 25, No. 11, pp. 2139-2147, 1998

Non Patent Literature 2
T. Li et. al., "Nonlinear Sinogram Smoothing for Low-Dose X-Ray CT" IEEE. Trans. Nucl. Sci., Vol. 51, No. 5, pp. 2505-2513, 2004

Patent Literatures

Patent Literature 1
WO2013/146283

DISCLOSURE OF THE INVENTION

Problems to be Solved by the Invention

According to the method as described in the Patent Literature 1, blurring at the edge of the structure within the subject may be prevented with reducing the streak artifacts. However, it is necessary to generate two images, i.e., the original image and the smoothed image, and this may cause a time-consuming problem in generating an image.

An objective of the present invention is to reduce streak artifacts and to generate an image of the structure in a subject with the edge of the structure being sharpened, within a short amount of time.

Means for Solving the Problems

In order to achieve the aforementioned objective, there is provided an X-ray CT system as the following, according to the present invention. The X-ray CT system of the present invention includes a raw data acquisition part configured to acquire raw data obtained by applying X-rays to a subject in imaging space and by detecting a distribution of X-ray strength passing through the subject, the raw data being associated with multiple views at different X-ray irradiation angles to the subject, an image reconstructor configured to apply a smoothing process to the raw data associated with multiple views, followed by image reconstruction to obtain a smoothed image of the imaging space, and a sharpening processor configured to apply more intense sharpening to pixels in a region of a central part of the subject in the smoothed image, relative to the pixels in a region of a peripheral part of the subject.

Advantage of the Invention

The present invention allows provision of an image showing the sharpened edge of the structure in the subject along with reducing streak artifacts in the image, within a short amount of calculation time.

BRIEF DESCRIPTION OF THE DRAWINGS

FIG. 5 is a flowchart showing an operation of a subject model generator of the X-ray CT system according to the second embodiment;

FIG. 8A illustrates arrangement of ellipses where three subject candidates are recognized in the vertical direction view and two subject candidates are recognized in the horizontal direction view, and FIG. 8B illustrates an example of arrangement where the subjects 11 appear to overlap one another when viewed from the vertical direction or from the horizontal direction;

BEST MODE FOR CARRYING OUT THE INVENTION

Figure 1:
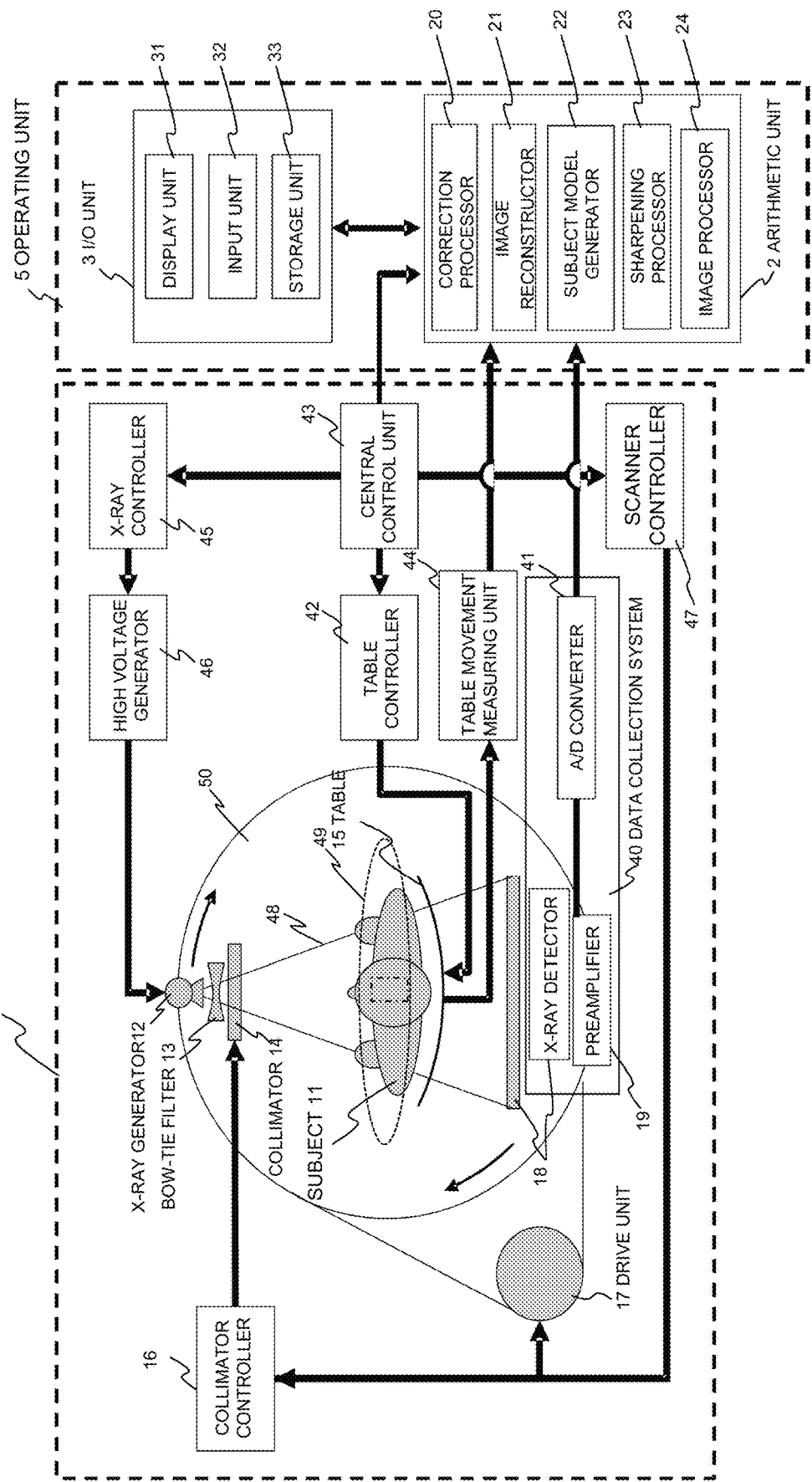
FIG. 1 is a block diagram showing a configuration of an X-ray CT system according to a first embodiment.

There will now be described embodiments of the present invention, with reference to the accompanying drawings. Hereinafter, in all the figures used for the following descriptions, elements with an identical function are labeled with the same reference numeral, and they will not be explained redundantly.

First Embodiment

Figure 2:
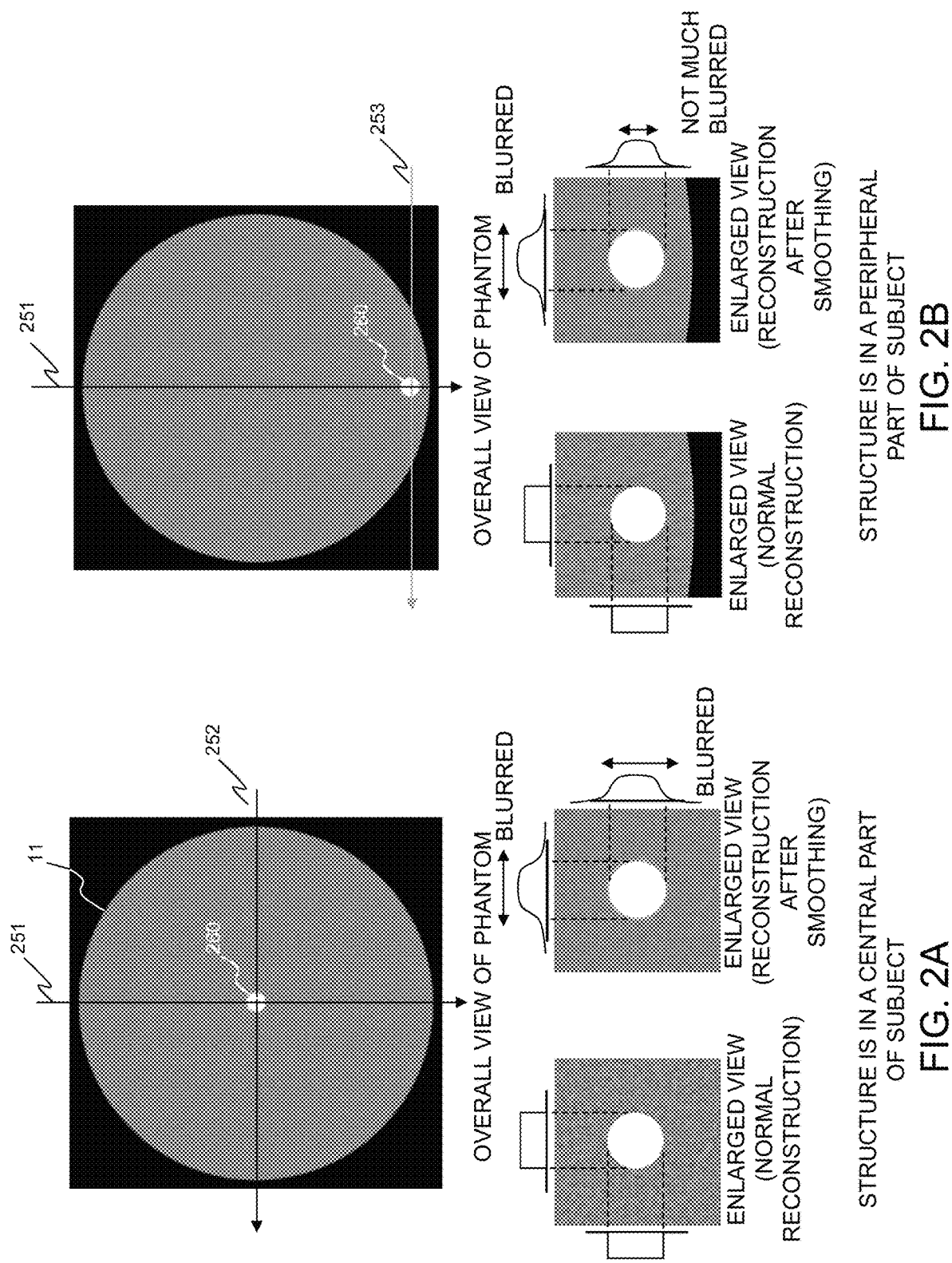
FIGS. 2A and 2B illustrate a structure positioned in a central part of a subject and the structure positioned in a peripheral part thereof, and reconstructed images.
Figure 3:
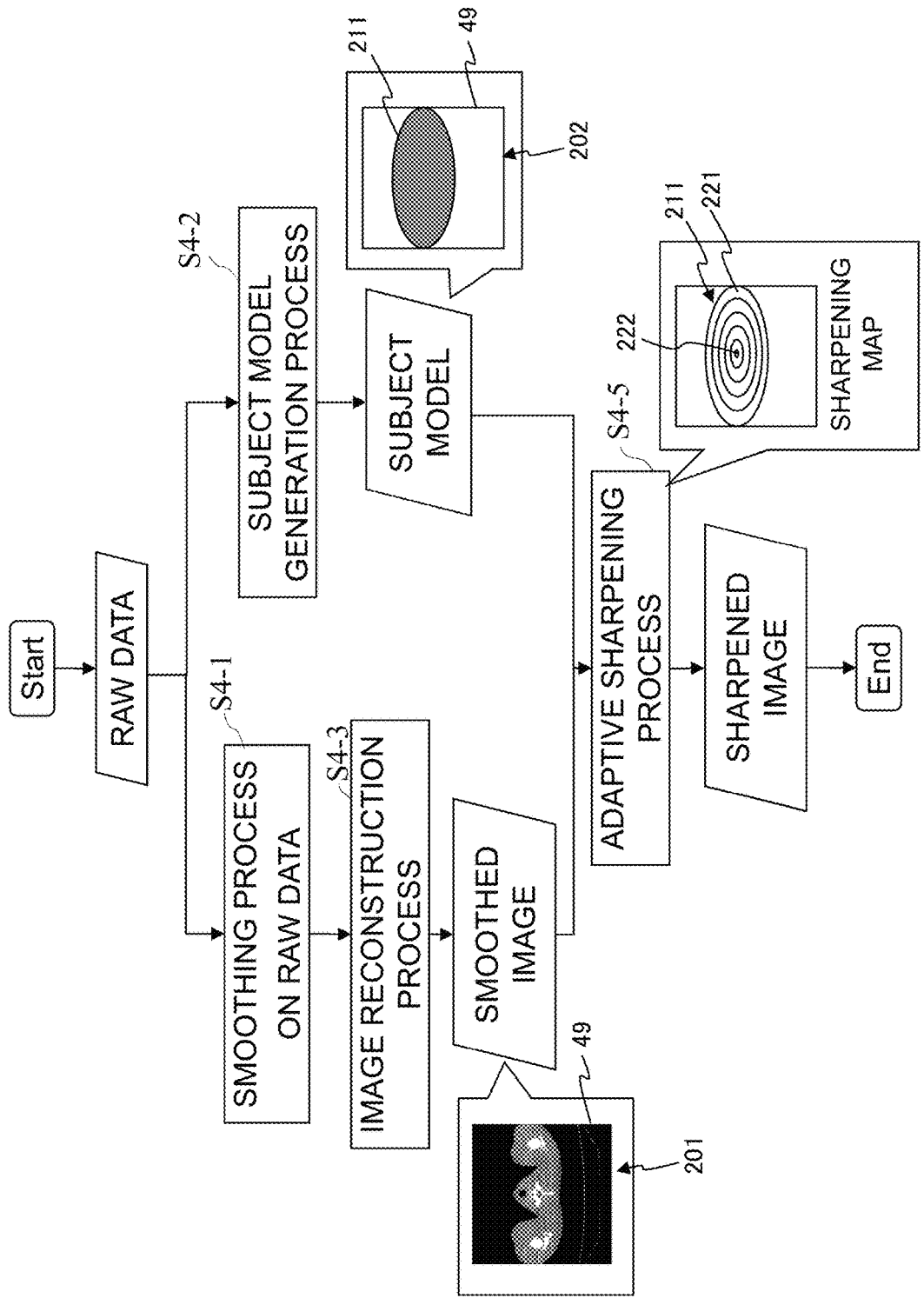
FIG. 3 is a flowchart showing a process of the X-ray CT system according to the first embodiment.

FIG. 1 is a block diagram showing an overview of the X-ray CT system of the present embodiment. FIGS. 2A and 2B illustrate a structure positioned in a central part of a subject and the structure positioned in a peripheral part thereof, and reconstructed images of the structure. FIG. 3 is a flowchart showing the process of the X-ray CT system.

As shown in FIG. 2A, X-rays passing through the structure 260 positioned in the central part of the subject 11 always pass through the center of the subject 11, when applied from any directions 251 and 252, allowing the X-ray to pass through the subject 11 for a long distance. On the other hand, as for the X-rays passing through the structure 260 positioned at the periphery part of the subject 11, there is a direction 253 that allows the X-ray to pass through the subject 11 for a short distance. The detected signals of the X-ray passing through the structure 260 positioned in the central part of the subject 11 are likely to include more noise than the detected signals of the X-ray passing through the structure 260 positioned in the peripheral part. Therefore, when the raw data is smoothed and reconstructed in response to the amount of noise, blurring at the edge of the structure positioned in the central part tends to be higher than the structure at the periphery part.

The present embodiment focuses on the problem above, and applies more intense sharpening process to the pixels in a region of the central part of the subject 11, than the pixels in a region of the peripheral part thereof, in an image (smoothed image) that is obtained by reconstructing the smoothed raw data. This process allows sharpening of the structure that is prone to high blurring in the central part of the subject.

More specifically, as illustrated in FIG. 1, the X-ray CT system of the present embodiment is provided with a raw data acquisition part 1, an image reconstructor 21, and a sharpening processor 23.

The raw data acquisition part 1 is configured to acquire raw data obtained by applying X-rays to a subject 11 in imaging space 48 and by detecting a distribution of X-ray strength passing through the subject 11, the raw data being associated with multiple views at different X-ray irradiation angles toward the subject.

The image reconstructor 21 applies the smoothing process to the raw data associated with multiple views (step S4-1 in FIG. 3), and then reconstructs an image (step S4-3), thereby generating a smoothed image 201 of a given region to be imaged 49 within the imaging space 48. This smoothing process can reduce noise impact on the raw data, allowing creation of the smoothed image 201 with reduced streak artifacts. The smoothing process, however, may cause blurring at the edge of the structure within the subject 11 in the smoothed image 201. Given this situation, in order to sharpen the blurring at the edge of the structure, the sharpening processor 23 applies more intense sharpening process to the pixels in the region 222 of the central part of the subject 11 in the smoothed image, than the pixels in the region 221 of the peripheral part of the subject 11 (step S4-5).

On this occasion, any method can be employed for identifying the central part and the peripheral part of the subject in the image. A user may enter an outline form of the subject, or the outline form of the subject may be obtained by applying an image processing to the smoothed image. In the present embodiment, in order to obtain the outline form of the subject with less calculation in a short time, a subject model 202 is created to represent the form and position of the subject, directly from the raw data (step S4-2 in FIG. 3).

Specifically, as shown in FIG. 1, the X-ray CT system of the present embodiment further includes a subject model generator 22. The subject model generator 22 creates a subject model 202 that represents in an approximate manner the form and position of the subject 11 in the region to be imaged 49, using one or more predetermined shape 211 and the position thereof (step S4-2). In other words, the subject model 202 represents the outline position of the subject in the region to be imaged 49, on the basis of the predetermined shape 211. In this case, the sharpening processor 23 brings the subject model 202 into correspondence with the smoothed image 201, and applies more intense sharpening process to the pixels in the region of the smoothed image 201 corresponding to the region 222 of the central part of the predetermined shape 211 of the subject model 202, than the pixels in the region of the smoothed image 201 corresponding to the region 221 of the peripheral part of the predetermined shape 211 (step S4-5). This allows more intense sharpening process on the pixels in the region 222 of the central part of the subject 11 within the smoothed image, than the pixels in the region of the peripheral part 221 of the subject 11.

In the present embodiment, in particular, the raw data of at least one view is selected from the raw data associated with multiple views acquired by the raw data acquisition part 1, and on the basis of a distribution of the signal strength of thus selected raw data, the subject model 202 is generated, representing the form and position of the subject 11 in the region to be imaged 49 in an approximate manner, using at least one predetermined shape 211 and the position thereof.

Accordingly, the subject model 202 can be created with less calculation within a shorter time, relative to the case where an image is reconstructed from the raw data as a first step, and then image processing is applied to determine the form and the like of the subject 11.

The predetermined shape 211 of the subject model 202 may be any form, and it may be an ellipse, for instance. In the case where an image of the subject 11 is generated including legs and arms, the shapes of both legs and both arms of the subject are approximated by ellipses, respectively, thereby generating the subject model 202, represented by multiple ellipses provided at the positions of those parts approximately.

The sharpening processor 23 increases a degree of sharpening process gradually and continuously from the peripheral part to the central part of the predetermined shape 211 of the subject model 202. When the subject model 202 includes more than one predetermined shape 211, the sharpening processor 23 increases a degree of sharpening process gradually and continuously from the peripheral part to the central part as to each of the predetermined shapes 211.

Upon generating the subject model 202 from the raw data of one view out of the raw data associated with multiple views, the subject model generator 22 projects a range where X-ray attenuation in the distribution of X-ray signal strength of the raw data increases sharply by the subject 11, to one axis of the predetermined shape (e.g., an ellipse) 211, thereby determining a diameter of the predetermined shape (ellipse) 211 in the axis direction. Then, a maximum value of the signal strength of the raw data may determine the diameter in the other axis direction. In addition, the diameter in the other axis direction may also be determined according to the area of the distribution of the signal strength of the raw data.

The subject model generator 22 may select raw data of two or more views to generate the subject model 202. In this case, the subject model generator 22 projects the range where X-ray attenuation in the distribution of X-ray signal strength of the raw data increases sharply by the subject 11, to one axis of the predetermined shape (e.g., an ellipse) 211 as to each view, thereby determining the diameter in the axis direction for each raw data. In this situation, the raw data of two or more views selected by the subject model generator 22 may include views in the vertical direction and in the horizontal direction, or views inclined at certain angles relative to the vertical direction and the horizontal direction. The two views are not necessarily orthogonal to each other.

As described so far, the X-ray CT system of the present embodiment reconstructs only the smoothed image and applies the sharpening process to thus reconstructed smoothed image, and this allows creation of an image within a short amount time, where the edge of the structure is sharpened along with reducing streak artifacts.

There will be given more specific descriptions in the following embodiments, i.e., the second embodiment and so on.

Second Embodiment

Figure 4:
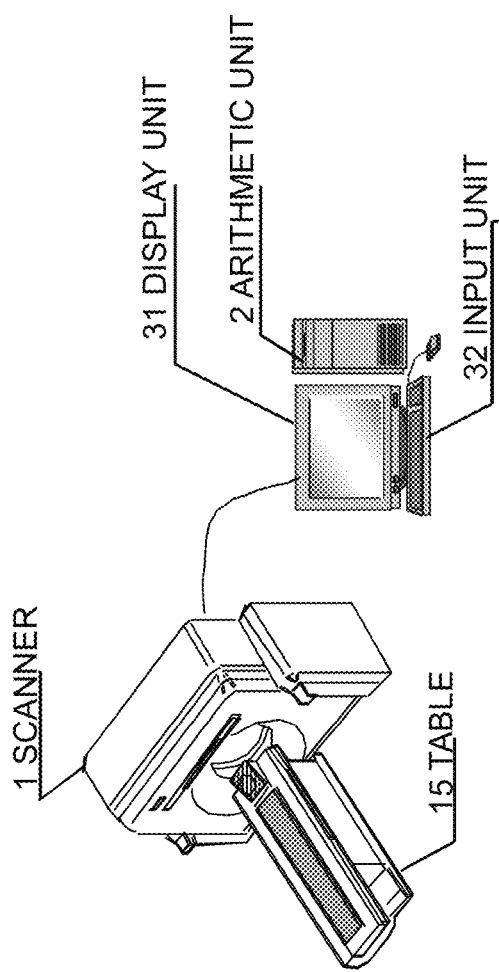
FIG. 4 is a perspective view of the X-ray CT system according to a second embodiment.

With reference to FIG. 4 and other related figures, there will be described the X-ray CT system of the second embodiment. The elements already described in the first embodiment are labeled with the same reference numerals, and redundant descriptions will not be provided.

FIG. 4 is a perspective view showing an outward appearance of the X-ray CT system according to the second embodiment. As illustrated in FIGS. 1 and 4, the X-ray CT system of the second embodiment is provided with a raw data acquisition part (hereinafter referred to as a scanner) 1, a table 15 for moving a subject placed thereon, an I/O unit 3, and arithmetic unit 2. The I/O unit 3 includes an input unit 32 comprising a mouse and a keyboard configured to input parameters for measurement and reconstruction, such as table moving speed information and a position for reconstruction, and a display unit 31 configured to display a reconstructed image and other information.

As illustrated in FIG. 1, the scanner 101 includes an X-ray generator 12, a high voltage generator 46, an X-ray controller 45, an X-ray detector 18, a scanner controller 47, and a central control unit 43. The high voltage generator 46 generates a certain current and high voltage to be supplied to the X-ray generator 12, under the control of the X-ray controller 45. With this configuration, X-ray generator 12 generates X-rays.

The X-ray generator 12 and the X-ray detector 18 are mounted on a disc 50 provided with an aperture (not illustrated) where the subject 11 is moved thereinto at the central portion. The disc 50 is connected to a drive unit 17 configured to drive the disc 50 rotationally. The disc 50 is further equipped with a Bow-tie filter 13 and a collimator 14 at the positions where X-rays generated from the X-ray generator 12 pass through. The collimator 14 is connected to a collimator controller 16. The scanner controller 47 is connected to the drive unit 17 for controlling rotation and stop of the disc 50, and to the collimator controller 16 for controlling an opening operation of the collimator 14.

The X-ray detector 18 is connected to a preamplifier 19 and an A/D converter 41 in this order.

The preamplifier 19 amplifies outputs from the X-ray detector 18, and the A/D converter 41 converts the outputs into digital signals, and delivers the digital signals to the arithmetic unit 2. The preamplifier 19 and the A/D converter 41 are also mounted on the disc 50. The X-ray detector 18, the preamplifier 19, the A/D converter 41 constitute a data collection system 40.

The table 15 incorporates a table driver to move the table 15 with respect to the disc 50. The table driver is connected to a table controller 42 for controlling the amount of driving, and to a table movement measuring unit 44.

The I/O unit 3 also comprises a storage unit 33 being arranged therein, in addition to the display unit 31 and the input unit 32. On the other hand, the arithmetic unit 2 is provided with a correction processor 20 and an image processor 24, in addition to the image reconstructor 21, the subject model generator 22, and the sharpening processor 23 as described in the first embodiment. The I/O unit 3 and the arithmetic unit 2 constitute an operating unit 5.

The arithmetic unit 2 comprises a computer incorporating a CPU and a memory, having a configuration where the CPU develops and activates predetermined programs stored in the memory, and implements by software the functions of the correction processor 20, the image reconstructor 21, the subject model generator 22, the sharpening processor 23, and the image processor 24. Alternatively, a part or all of the above functions of the arithmetic unit 2 may be implemented by hardware. By way of example, a circuit may be designed to configure the arithmetic unit 2 using custom IC such as ASIC (Application Specific Integrated Circuit) and programmable IC such as FPGA (Field-Programmable Gate Array), and thereby implementing a part or all of the functions of the correction processor 20, the image reconstructor 21, the subject model generator 22, the sharpening processor 23, and the image processor 24.

Operations of each part will be described. When the operator inputs from the input unit 32 of the operating unit 5, imaging conditions (including the table moving speed, tube current, tube voltage, and slice position), and reconstruction parameters (including ROI, a reconstructed image size, a view width, a reconstruction filter function, and an image thickness in the body axis direction), the central control unit 43 outputs according to the instructions above, control signals necessary for imaging to the X-ray controller 45, the table controller 42, and the scanner controller 47. With this configuration, when the operator manipulates the input unit 32 to output an imaging start signal, imaging is started. Upon starting the imaging, the X-ray controller 45 transmits control signals to the high voltage generator 46, high voltage is applied to the X-ray generator 12, and the subject 11 is irradiated with X-rays from the X-ray generator 12. Simultaneously, the scanner controller 47 transmits control signals to the drive unit 17, thereby rotating the disc 50. Then, the units such as the X-ray generator 12, the X-ray detector 18, and the preamplifier 19 turnaround the subject 11. On the other hand, according to the control by the table controller 42, the table 15 with the subject 11 placed thereon moves in parallel with the body axis direction, or stops moving.

The bow-tie filter 13 shapes X-ray beams of the X-rays emitted from the X-ray generator 12, then the collimator 14 restricts a radiation field thereof, and then, the subject 11 is irradiated with the X-rays. The X-rays are absorbed (attenuated) by each of the structures within the subject 11, passing through the subject 11, and detected by the X-ray detector 18. The detection timing corresponds to the time when the disc 50 turns only at a predetermined angle in the rotating direction. The unit of the data collection in the direction of rotation is referred to as a "view". The X-ray detector 18 has a configuration that detector elements are arranged two-dimensionally. The array of elements along the rotating direction of the disc 50 is referred to as a channel direction, and the body axis direction of the subject 11 orthogonal thereto, is referred to as a column direction. Collected data is identified on the basis of the views, channels, and columns.

The X-rays detected by each of the detector elements in the X-ray detector 18 are converted into current, amplified by the preamplifier 19, further converted into digital signals by the A/D converter 41, and then outputted to the arithmetic unit 2.

The correction processor 20 in the arithmetic unit 2 applies following processing to the digital signals from the A/D converter 41, the processing including an offset correction process for correcting an offset of the output due to dark current from the detector elements, an air correction process, a reference correction process, a logarithmic transformation process, and a phantom calibration process for preventing a beam hardening effect. Data after those corrections are applied is stored in the storage unit 33 in the I/O unit 3, in the form of actually measured raw data.

Next, with reference to the flowchart of FIG. 3, there will now be described operations of the image reconstructor 21, the subject model generator 22, and the sharpening processor 23 in the arithmetic unit 2.

First, in step S4-1, the image reconstructor 21 applies a smoothing filter to the raw data of each view stored in the storage unit 33, and obtains smoothed raw data. Next, in step S4-3, image reconstruction is performed using the smoothed raw data, and there is obtained reconstructed image (smoothed image) 201 of the region to be imaged 49 within the imaging space 48. It is desirable this smoothing filter should be a filter that permits variations in smoothing intensity in response to the signal strength of the raw data. A publicly known method including the methods as described in Non Patent Literatures 1 and 2 maybe applied to this smoothing process. As a method of the image reconstruction performed by the image reconstructor 21, a widely known method may be used. For example, with convolution of the reconstruction filter in the channel direction as to each view and each column, a back projection process is performed being weighted in the direction of view, thereby obtaining a reconstructed image in the form of a distribution chart of X-ray attenuation coefficient within the subject in the region to be imaged 49. Accordingly, since the raw data is subjected to smoothing process in advance, a reconstructed image (smoothed image 201) where streak artifacts have already been reduced can be obtained.

In step S4-1, if the smoothing process is performed according to the method as described in the Non Patent Literature 2, it is necessary to set smoothing strength parameters acting commonly on all the detector elements in the X-ray detector 18. Therefore, preferably, a freely selected strength parameter may be discretized to determine levels of L stages of smoothing strength, such as 1, 2, 3, . . . and L (hereinafter, referred to as smoothing level), and a relationship between the levels and the smoothing strength parameters is stored in the storage unit 33. In this case, the operator selects a level of the smoothing strength via the input unit 32, and the image reconstructor 21 accepts the level selected by the operator, reads the smoothing strength parameter associated with the level thus selected by the operator, and performs the smoothing process at the strength.

As described above, when the smoothing process is applied to the raw data, not only impact of noise in the detected signals may be reduced, but also abrupt change in the detected signal values may be smoothed at the edge part of the raw data, corresponding to the structure having relatively high contrast within the subject 11. Therefore, there is a problem that blurring is prone to occur at the edge of the high contrast structure within the subject in the reconstructed image. Accordingly, in the present embodiment, in order to overcome this shortcoming, the sharpening processor 23 applies a sharpening process to the smoothed image 201 in the image space, thereby restoring the image of the structure from blurring. In other words, the sharpening processor 23 applies more intense sharpening process to the pixels in the region 222 of the central part of the subject within the smoothed image, than the pixels in the region 221 of the peripheral part, in order to sharpen the blurring at the edge of the structure.

In the present embodiment, the subject model generator 22 creates the subject model 202 representing approximately the shape and position of the subject 11 in the region to be imaged 49, by using one or more predetermined shapes 211 and the position or positions thereof, on the basis of a distribution of signal strength of the raw data. Accordingly, the positions of the region 222 of the central part and the region 221 of the peripheral part 221 in the subject can be figured out within the short amount of time, allowing the sharpening process to be performed.

In other words, in the present embodiment, levels of signal reduction (blurring) in the smoothed image 201 are modeled according to the concepts as the following:
a) The signal reduction levels at freely selected points in the image space are averaged in the angle direction, and then, position dependency of the signal reduction is noted.
b) In order to reduce calculations, under the assumption that a figure of the subject 11 in the smoothed image can be approximated by one or more ellipses, an image of the subject 11 is modeled by ellipses to create the subject model 202. The signal reduction level is assumed to be identical on concentric ellipses, as to each of one or more ellipses 211. Since the action caused by the subject 11 for attenuating X-rays becomes more intensive with approaching the central part of the subject 11 from the periphery part thereof, the structure in the central part of the subject 11 suffers from larger signal reduction of the raw data, than the structure in the peripheral part. This causes increased noise ratio in the structure in the central part, and eventually, this intensifies the smoothing on the edge of the raw data according to the smoothing filter. c) The total number, the positions, and the dimensions (lengths of long and short axes) of the ellipses in b) above are calculated, on the basis of the raw data of one or more views (the raw data of views in a vertical direction and in a horizontal direction, as the simplest example).

Specifically, in step S4-2, the subject model generator 22 generates the subject model 202. With reference to the flowchart as shown in FIG. 5, the process of generating the subject model 202 in step S4-2 will be described. First, in step S5-1, the subject model generator 22 selects at least one raw data from the raw data associated with multiple views. In the present embodiment, the subject model generator 22 selects two views, a vertical direction view (a view when the X-ray tube is the closest to 12 o'clock position or to 6 o'clock position), and a horizontal direction view (when the X-ray tube is closest to 3 o'clock position or to 9 o'clock position). As to each of the views thus selected, for the case of imaging by axial scanning, the subject model generator 22 selects an array of detector elements at the position being closest to the body axis direction (hereinafter, referred to as image slice position) of an image to be generated at the rotation center. For the case of radial scanning, the subject model generator 22 selects the center column (an average of central two columns if the detector has even number of columns). Any other method may be applicable in selecting the detector elements in the column direction, as far as the raw data reflecting an outline of the subject in the image slice position can be obtained.

Figures 6A, 6B:
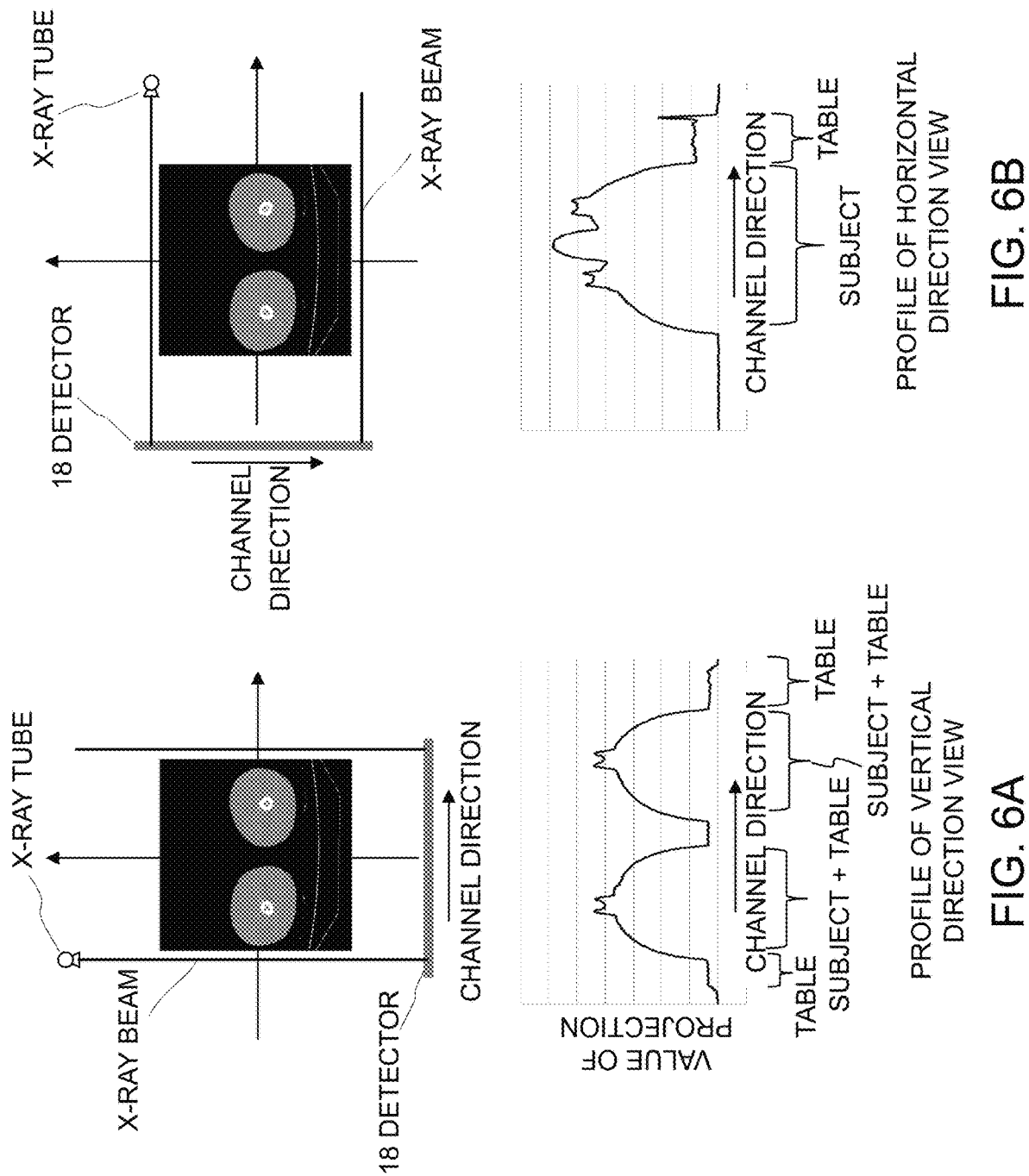
FIGS. 6A and 6B illustrate imaging directions and data profiles of raw data, in a vertical direction view and in a horizontal direction view according to the second embodiment.

Next, in step S5-2, the subject model generator 22 creates a profile of the raw data (detected signals) in the channel direction, for each of the selected views in the vertical and horizontal directions. FIGS. 6A and 6B illustrate sets of a conceptual diagram of the imaging direction and a profile of raw data, respectively in the vertical direction and in the horizontal direction, with regard to a phantom that simulates both legs of human body. Since the image slice in the image of the subject 11 is positioned at both legs, the image of the subject 11 is separated into two parts. The vertical profile of raw data shows two bell-like curves, whereas the horizontal profile shows one bell-like curve since the raw data items of the subject's legs overlap one another.

In step S5-3, the subject model generator 22 identifies an image of the subject 11, according to the profile of the raw data. In this situation, imaging is performed including the table 15 in proximity to the subject 11. Since it is not necessary to sharpening an image of the table 15, the raw data profile of the table and the raw data profile of the subject should be distinguished from one another on the basis of a value of projection (detected signal value), so as to identify only the image of the subject 11. Therefore, the image of the table 15 is taken in advance to obtain the value of projection, under various imaging conditions, such as the position of the table, and tube voltage and tube current of the X-ray generator 12. Then, a minimum threshold (table threshold) is obtained to distinguish the value of projection of the table 15 from the value of projection of the subject 11, and thus obtained threshold is stored in the storage unit 33. Then, in step S5-3, as shown in FIG. 7A, the subject model generator 22 scans the values of projection in the profile of the vertical direction view in ascending order from the smallest channel number, and the channel number of the value of projection exceeding the table threshold is set to $v_1^{(s)}$ and it is stored in the storage unit 33. The subject model generator 22 further continues scanning, and the channel number obtained by subtracting one from the channel number of the value of projection, equal to or less than the table threshold, is set to $v_1^{(e)}$ and stored in the storage unit 33. Similarly, the subject model generator 22 continues scanning, the channel number of the value of projection that exceeds the table threshold next is set to $v_2^{(s)}$, and the channel number obtained by subtracting one from the channel number of the value of projection equal to or less than the table threshold is set to $v_2^{(e)}$ and stored in the storage unit 33. The steps as described so far are generalized, and the subject model generator 22 identifies the channel numbers $v_n^{(s)}$ to $v_n^{(e)}$ of the profile, as corresponding to the n-th "subject candidate". The same process as described above is applied to the horizontal direction view, and the subject model generator 22 identifies the channel numbers $h_n^{(s)}$ to $h_n^{(e)}$ where the values of projection exceed the threshold, as corresponding to the "subject candidate", and stores those channel numbers in the storage unit 33.

Next, in step S5-4, the subject model generator 22 generates an ellipse on the basis of the channel numbers of the subject candidate. First, the number of the subject candidates identified in the vertical direction view is multiplied by the number of the subject candidates identified in the horizontal direction view, thereby obtaining the total number of the subject candidates, and then, each subject 11 is identified by the serial number m. The ellipses 211 are provided respectively for m subjects 11. For example, FIG. 8A illustrates that three subject candidates are identified in the horizontal direction view, whereas two subject candidates are identified in the vertical direction view. In this example, the number of the subjects 11 is recognized as six, and thus total number of the ellipses is six. However, as shown in in FIG. 8B, when the subjects 11 are arranged in a manner that the subjects overlap one another when viewed from the vertical direction or from the horizontal direction, resulting in that the ellipses 211 are provided in the positions where the subject 11 does not exist actually. In this case, the ellipses at the positions where the subject 11 does not exist actually are provided erroneously. However, considering that there is neither a target for diagnosis nor a structure to be emphasized in the air region (or only the table is included), the ellipses 211 at the erroneously identified positions are also provided in this example.

Next, the subject model generator 22 determines the central position and the size of each ellipse 211. For the sake of simplification, the ellipse 211 is provided with the setting of two axes, in the vertical and horizontal directions in this example, but the ellipse 211 can be oriented to any direction.

Focusing on the m-th subject candidate in the profile of the vertical direction view, the channel positions of the channel numbers $v_m^{(s)}$ and $v_m^{(e)}$ on the detector 18, with aligning the center thereof with the rotation center of the disc 50, are given by $d(v_m^{(s)}-(A-1)/2)$ and $d(v_m^{(e)}-(A-1)/2)$, where the size of the element per channel is d (mm) and the number of channels of the detector 18 is A (noting the count of the channel number starts from zero). In addition, the central position $c_m^v$ (mm) of the subject candidate m is given by the following equation, representing an average value of the channel positions of the channel numbers from $v_m^{(s)}$ to $v_m^{(e)}$:

$$c_m^v = d(v_m^{(s)} + v_m^{(s)} - A + 1)/2 \quad (1)$$

Similarly, as for the m-th subject candidate in the profile of the horizontal direction view, the central position $c_m^h$ (mm) is given by the following equation:

$$c_m^h = d(h_m^{(s)} + h_m^{(e)} - A + 1)/2 \quad (2)$$

As described above, in the subject model generator 22, the axis directions of the ellipse 211 are aligned with the vertical direction view and the horizontal direction view, and thus if the coordinates in the horizontal and vertical directions are represented by $(e_1, e_2)$, the center coordinates of the m-th ellipse is represented by $(c_m^v, c_m^h)$.

In addition, if the length of the horizontal axis ($e_1$ axis) of the m-th ellipse 211 is represented by $r_m^v$, $r_m^v$ is given by the following equation, using the channel numbers in the vertical direction view associated with the m-th subject candidate:

$$r_m^v = d(-v_m^{(s)} + v_m^{(e)})/2 \quad (3)$$

Similarly, if the length of the vertical axis ($e_2$ axis) of the m-th ellipse 211 is represented by $r_m^h$, $r_m^h$ is given by the following equation, using the channel numbers in the horizontal direction view:

$$r_m^h = d(-h_m^{(s)} + h_m^{(e)})/2 \quad (4)$$

According to Equations 1 to 4, the coordinates and size of all the m ellipses 211 are obtained, and they are arranged in the region to be imaged 49, whereby the subject model 202 can be created (step S5-4). It should be noted the range in the region to be imaged 49 in the horizontal and vertical directions may agree with the channel range of the X-ray detector 18 in the horizontal and vertical direction views, or the ranges may not necessarily be identical as far as the correspondence therebetween is known.

The subject model generator 22 calculates the aforementioned coordinates and size of the ellipse 211, as to each of image slices (the unit of image in the body axis direction), and creates a three-dimensional subject model 202.

Referring to the flowchart of FIG. 3 again, processing of the sharpening processor 23 will be described. In step S4-5, the sharpening processor 23 uses the subject model 202 to apply the sharpening process to the smoothed image 201. First, focusing on the j-th pixel in the smoothed image 201, if a ratio of similitude of the concentric ellipses passing through the pixel center $(x_1, x_2)$ is $w_{j,m}$ for the m-th ellipse (the dimension $(r_m^v, r_m^h)$ with the center coordinates $(c_m^v, c_m^h)$ and the axis $(e_1, e_2)$) of the subject model 202 created in step S4-2, the ratio of similitude $w_{j,m}$ is given by following equation 5:

$$w_{j,m} = \{(x_1 - c_m^v)/r_m^v\}^2 + \{x_2 - c_m^h)/r_m^h\}^2 \quad (5)$$

In here, the closer to zero is the ratio of similitude $w_{j,m}$, the j-th pixel is closer to the center coordinate $(c_m^v, c_m^h)$ of the ellipse 211, whereas the ratio of similitude $w_{j,m}$ is closer to one, the j-th pixel is closer to the periphery of the ellipse 211. When the ratio of similitude $w_{j,m}$ exceeds one, the center of the j-th pixel is outside the ellipse 211.

In the present embodiment, the levels of signal reduction (blurring) of the structure in the smoothed image 201 caused by the smoothing process in S4-1, are approximated by multiple concentric ellipses with various distance from the center of the ellipse 211 of the subject model 202, and sharpening strength increases in the pixels that are closer to the center of the ellipse 211, where the ratio of similitude of the ellipse 211 is closer to zero. In this situation, according to a T-th degree polynomial $\Psi_L(w_{j,m})$ where the smoothing level of the smoothing filter used in S4-1 is L, the sharpening strength for the ratio of similitude $w_{j,m}$ is given by following equation 6:

$$\Psi_L(w_{j,m}) = \Sigma_{t=0}^{T} a_{t,L} w_{j,m}^t \quad (6)$$

In Equation 6, t denotes the degree of the polynomial, $w_{j,m}^t$ represents t-th power of the ratio of similitude $w_{j,m}$ obtained by Equation 5, and $a_{t,L}$ denotes the predefined coefficients for the corresponding terms of the degree and of the smoothing level.

Furthermore, non-negativity constraint is provided to $\Psi_L$ (wj, m) in Equation 6, as given in the following equation, and $\tilde{\Psi}_L$ (wj, m) is obtained, noting $\tilde{\Psi}$ represents the sign having "~" above $\Psi$:

$$\tilde{\psi}_L(r_{j,m}) = \max(\psi_L(r_{j,m}), 0) \quad (7)$$

Equation 7 expresses when a value of $\Psi_L(w_{j,m})$ is negative, it is replaced by zero, so as to avoid the sharpening process. That is, when a pixel of interest is outside the ellipse 211, the value of $\Psi(w_{j,m})$ is negative, and the value is replaced by zero according to Equation 7.

The value of $\Psi_L(w_{j,m})$ may be obtained experimentally, or it may be calculated according to numerical simulation. In the present embodiment, an example employing the latter will be described later.

Next, let K $(w_{j,m}, L)$ denote the sharpening strength of the pixel j, and the sharpening strength $K(w_{j,m}, L)$ is given by following Equation 8:

$$\kappa(w_{j,m}, L) = \tilde{\psi}_L(w_{j,m}) \quad (8)$$

The sharpening strength above is calculated per pixel, but in some cases, those values may become extremely discontinuous in the slice direction, when the accuracy of the subject model 202 is low due to the reason that the subject model 202 is created on the image slice basis in step S4-2. To address this problem, a publicly known smoothing filter (Gaussian filter, or similar filters) may be used to average (obscure) the sharpening strength in the body axis direction, thereby mitigating this discontinuity.

The sharpening processor 23 applies the publicly known sharpening process to the smoothing image 201 in step S4-5, using the sharpening strength $\kappa$ $(w_{j,m}, L)$ as to each pixel j, given by Equation 8, and generates a sharpened image. For example, as the sharpening process, the pixel value of the pixel j is multiplied by the sharpening strength $\gamma(w_{j,m}, L)$ of Equation 8. Accordingly, an image thus sharpened can be obtained. The sharpening processor 23 stores the obtained sharpened image in the storage unit 33 and also displays the image on the display unit 31.

The image obtained by the sharpening process may further be added to the smoothed image, so as to obtain the sharpened image. As the sharpening process, in addition to the method of multiplying the pixel value by the sharpening strength, publicly known methods may be applicable, such as processing using the Sobel filter and Unshaped Mask.

When an operator instructs via the input unit 32, to perform image processing such as change of the displayed slice, on the sharpened image that is displayed on the display unit 31, the image processor 24 executes the process requested by the operator.

There will now be described a method for calculating the sharpening strength $\Psi_L (w_{j,m})$ as represented by Equation 6, according to numerical simulation. As shown in FIG. 2, a numerical phantom is made, simulating a water cylinder that contains a small structure. In this situation, various types of numerical phantoms are made, with shifting the position of the structure from the center of the cylinder. CT imaging is simulated using these numerical phantoms, and raw data is generated. A normal image reconstruction process is applied to the generated raw data, and an image (hereinafter, referred to as normal reconstructed image) is generated. Furthermore, the smoothing process described in S4-1 is applied to thus generated raw data at a freely selected smoothing level, and then the image reconstruction process is applied to generate a smoothed image.

By comparing the structure edge in the normal reconstructed image with that in the smoothed image, signal reduction is converted into a numerical form. For this numerical expression, a publicly known method can be applied. For example, frequency components of an edge-spread function are integrated to obtain a signal value of the edge. This measurement is performed on each of various numerical phantoms with different positions of the structure, allowing the plotting of signal reduction, as the position of the structure changes from the center to the periphery of the water cylinder. In addition, the plotting is approximated by the polynomial, the coefficients $a_{t,L}$ of the sharpening strength function $\Psi_L (w_{j,m})$ are calculated, at every certain distance from the center of the ellipse 211. It is to be noted the signal reduction levels are calculated in advance, in association with the smoothing levels L that are selectable by the operator in the processing described above, because the level of the signal reduction at the edge of the structure varies in response to the smoothing level of the smoothing filter.

Third Embodiment

There will now be described the X-ray CT system of the third embodiment.

Figure 9:
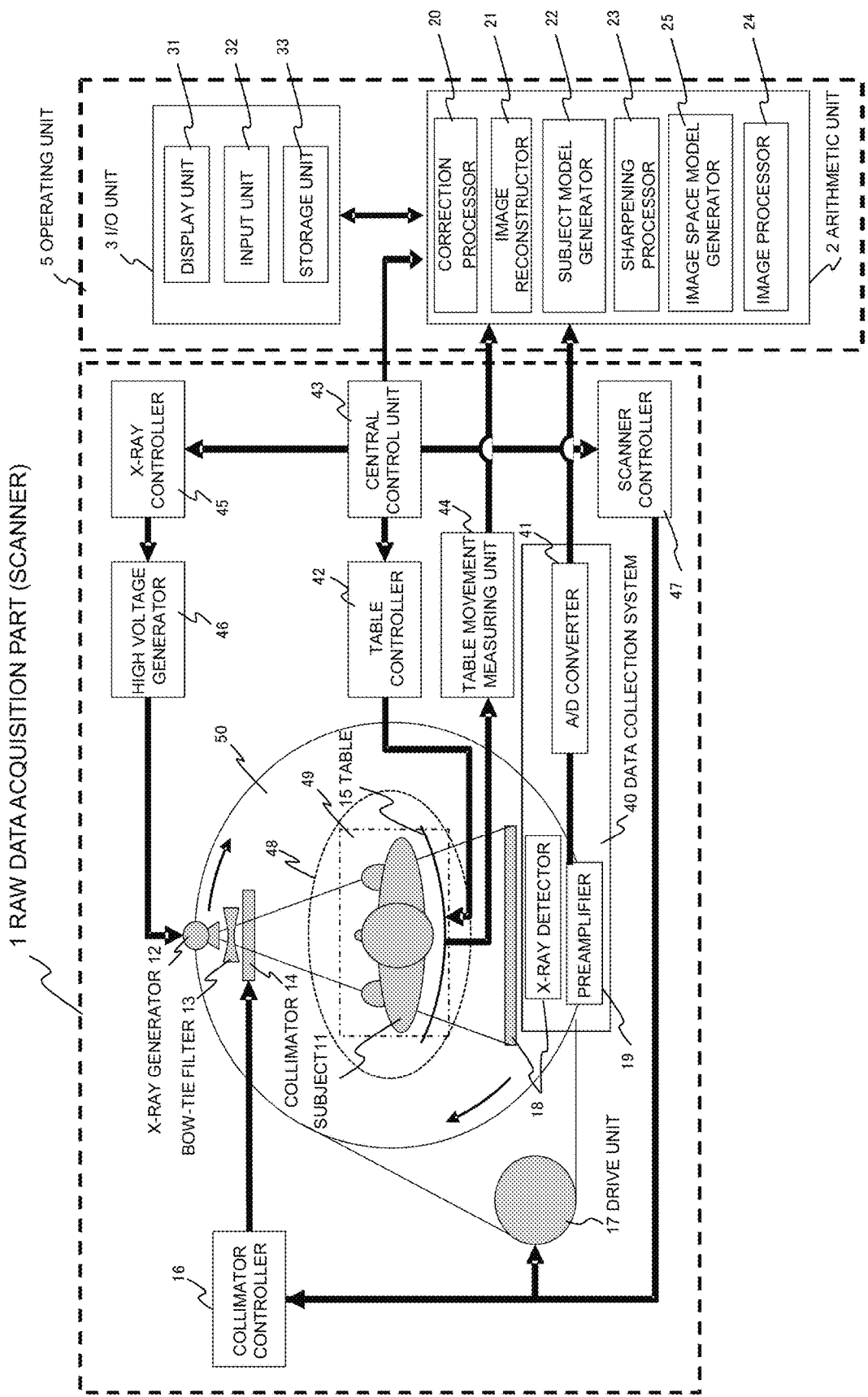
FIG. 9 is a block diagram showing a configuration of the X-ray CT system according to a third embodiment.

In the second embodiment, the shape of the subject 11 is approximated by the ellipse 211, so as to create the subject model 202, but in approximating the actual subject 11, there may be found some disagreement in the shape of the ellipse 211, in approximating the actual subject 11. Since X-ray detection strength changes abruptly around the body surface or bones of the subject 11, the signal reduction level varies significantly in response to such changes. Therefore, around the body surface or bones of the subject 11, the disagreement in shapes between the ellipse 211 and the subject 11 may have significant impact on the image quality. For example, around the body surface of the subject 11, adjacent detector elements may detect the X-rays passing through the subject 11, and the X-rays passing through the air, respectively. Therefore, when the ellipse 211 being provided is larger than the region of the actual subject 11, the signal reduction level is likely to be overestimated. Under these circumstances, the sharpening process performed on the basis of the information of this ellipse 211 may result in that the edge corresponding to the subject's body surface may be emphasized too much in the image. To address this problem, in the present embodiment, as shown in FIG. 9, the arithmetic unit 2 is further provided with a pixel-value variation calculator configured to obtain a degree of variation (change) of the pixel values between the pixels that are adjacent to each other in the smoothed image. The sharpening processor 23 reduces the rate of sharpening for the pixel with a high degree of variation in pixel value, relative to the pixel with a low degree of variation in pixel value.

Figure 10:
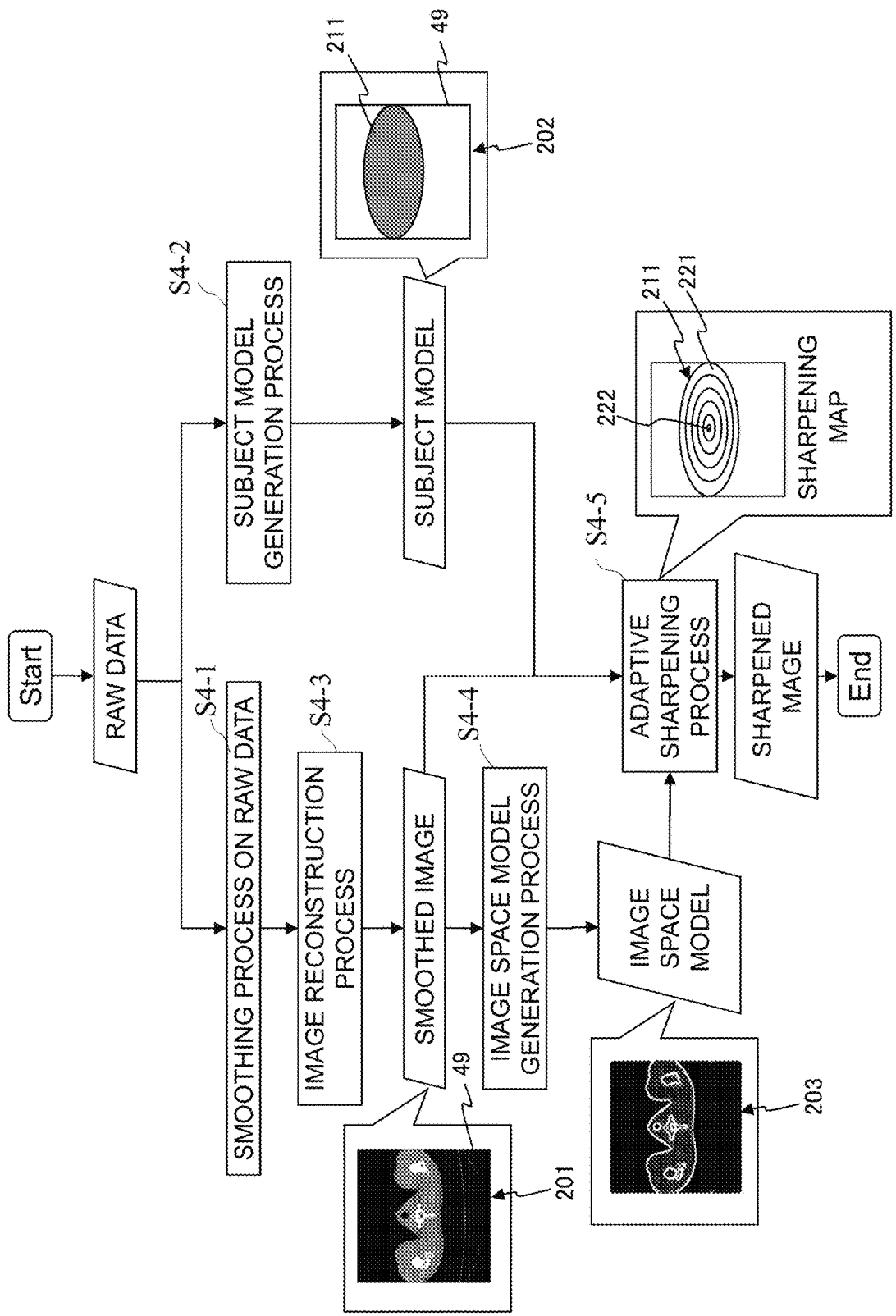
FIG. 10 is a flowchart showing a process of the X-ray CT system according to the third embodiment.

As indicated by the flowchart of FIG. 10, after the image reconstructor 21 generates the smoothed image 201 in steps S4-1 and 4-3 in the same way as the first embodiment, the image space model generator 25 creates the image space model in step S4-4. The image space model indicates a distribution of the pixel value variation between adjacent pixels in the smoothed image. The sharpening processor 23 changes the rate of sharpening, in response to the distribution of pixel value variation of the image space model.

Specifically, the image space model generator 25 reads the smoothed image 201, and scans the rectangular kernel with any size of p×p on the smoothed image 201. Then, as to each of the pixel included in the rectangular kernel, the pixel value (CT value) of the smoothed image 201 is determined on the basis of a threshold, and the pixels are categorized into three groups, air, water, and bone. In other words, predefined two thresholds are provided (hereinafter, referred to as image model threshold 1 and image model threshold 2). A pixel having a CT value smaller than the image model threshold 1 is determined as air, a pixel having a CT value equal to or larger than the image model threshold 1 and less than the image model threshold 2 is determined as water, and a pixel having a CT value equal to or larger than the image model threshold 2 is determined as bone. The image model threshold 1 may be set to any value within the range of general CT values indicating air and water (−1000 HU and 0 HU) (assuming components around the body surface of human body as water), and it may be set to −500 HU, for instance. Similarly, the image model threshold 2 may be set to any value within the range of general CT values indicating water and bone (0 HU and 1000 HU), and it maybe set to 500 HU, for instance. In some cases, the CT value of bone may be around 400 HU, depending on bone density, and other conditions. However, in this case, it is only needed to identify abrupt change in CT value, and thus the value of 1000 HU showing the contrast between water and air was also assumed as the contrast between water and bone, in this example.

Next, as to each of the three categories, the number of pixels is counted within the kernel, and the number of pixels $S_U$ categorized as air or bone and the number of pixels $S_L$ categorized as water are calculated. Furthermore, the ratio $u_j$ is given by the following equation, where the index of the pixel of interest is j and the ratio of the number of pixels indicating air or bone of the total number of pixels across the kernel is $u_j$:

$$u_j = S_U/(S_U + S_L) \qquad (9)$$

Equation 9 indicates the closer to zero or to one becomes the value of the ratio $u_j$, the less spatial variation in the CT value is found in proximity to the pixel j, whereas the closer to 0.5 becomes the value of the ratio $u_j$, more abrupt change in the CT value is found in proximity to the pixel j. Accordingly, using the ratio $u_j$ as an index, a pixel where detection strength abruptly changes is identified, and it is possible to prevent unnatural sharpening that occurs due to disagreement between the subject 11 and the ellipse 211 of the subject model 202.

FIG. 10 shows the image space model 203 being an image where white represents the pixels with the value of the ratio u close to 0.5, and black represents the pixels with the value of the ratio $u_j$ equal to zero or close to one. As obvious from FIG. 10, in the image space model 203, the outline of the subject 11, and the outline of the structure (bones in this example) are shown in white.

It should be noted that the rectangular kernel may be expanded three-dimensionally to p×p×p, or the size of the kernel may be defined in a manner that standardizes the spatial size of the pixel according to the following expression:

$$p_1 \times p_2 \times p_3 (\forall p_1, p_2, p_3) \quad (10)$$

where p1, p2, and p3 represent kernel sizes in the image section, respectively in the lateral direction, in the longitudinal direction, and in the slice direction.

Next, on the basis of the image space model 203 created in step S4-4, the sharpening processor 23 reflects the ratio $u_j$ being the index of abrupt CT value change around the pixel of interest j, on the sharpening strength in step 4-5. Here, when the value of the ratio u in the pixel j is close to zero or close to one, spatial variation in CT value is small. Therefore, even though the sharpening strength increases, the disagreement between the outline of the subject 11 and the ellipse 211 of the subject model 202 hardly appear in the image. On the other hand, when the value of the ratio $u_j$ in the pixel j approaches 0.5, abrupt change in CT value is liable to occur. Therefore, when the sharpening strength increases, the disagreement between the subject 11 and the ellipse 211 of the subject model 202 remarkably appears in the image. Given these circumstances, the sharpening processor 23 uses a continuous function (u) that outputs one when the value of the ratio $u_j$ is zero or one, and that outputs zero when the value of the ratio $u_j$ is 0.5, so as to adjust the sharpening strength according to the function $\eta(u_j)$. In here, Equation 11 in the following is employed as the function $\eta(u_j)$:

$$\eta(u_j) = 4(u_j - 0.5)^2 \quad (11)$$

For the sake of simplicity, a quadratic function is employed as the function $\eta(u_j)$ in this example, but any function may be used if the function satisfies the conditions above.

The sharpening processor 23 uses the function $\eta(u_j)$, and the sharpening strength $\gamma(w_{j,m}, u_j, L)$ in the pixel j is given by Equation 12:

$$\gamma(w_{j,m}, u_j, L) = \ddot{\psi}_L(w_{j,m}) \gamma(u_j) \quad (12)$$

The sharpening processor 12 uses the sharpening strength $K(w_{j,m}, u_j, L)$ represented by Equation 12, so as to perform the sharpening process, whereby in the pixel at the position of the outline of the subject 11 with the value of the ratio u' 0.5, the function $\eta(u_j)$ becomes zero, the sharpening strength $\kappa(w_{j,m}, u_j, L)$ also becomes zero, and accordingly, the sharpening process is not performed. Therefore, unnatural sharpening of the outline of the subject 11 can be prevented.

Since the steps such as step S4-1 and S4-2 other than the steps described above are performed in the same way as the second embodiment, detailed description will not be given in here.

As described above, the sharpening strength used by the sharpening processor 23 for the sharpening is calculated as to each pixel. However, since the subject model 202 is created on the image slice basis, the sharpening strength may take extremely discontinuous values in the slice direction, when a degree of matching is low between the subject model 202 and the subject 11. To address this problem, a publicly known smoothing filter (Gaussian filter, or similar filters) may be used to average (obscure) the sharpening strength in the body axis direction, thereby mitigating this discontinuity.

Fourth Embodiment

There will now be described the X-ray CT system according to the fourth embodiment.

As described in step S5-1 to S5-4 with reference to FIGS. 6A and 6B, in the second embodiment, the subject model generator 22 has a configuration to select raw data of the views in the vertical and horizontal directions and to set the ellipse 211 thereon. In the present embodiment, the subject model generator selects views angled with respect to the vertical and horizontal directions (hereinafter, referred to as a horizontal oblique view and a vertical oblique view), and sets the ellipse 211 having the axial directions in the vertical and horizontal directions.

With the horizontal oblique view and the vertical oblique view, the ellipse 211 of the subject 202 can be created, even when the raw data of the views in the vertical and horizontal directions is not included in the view range of the raw data that is used for creating an image of interest. For example, when the view range of the raw data used for creating the image of interest is positioned around the time of imaging start or imaging end, there is a possibility that no raw data is found in association with the vertical direction or the horizontal direction, at the closest to the point of the imaging start or the imaging end. In this case, the vertical direction view or the horizontal direction view at a distance from the image of interest in the body axis direction may be used instead. However, the time of imaging and the position in the body axis direction may be displaced with respect to the image of interest. In the present embodiment, the raw data of oblique views is selected, and thus the displacement above may be prevented, thereby allowing a setting of the ellipse 211 with higher degree of accuracy.

In addition, since the raw data of the view inclined from the horizontal direction is used, this may reduce the length of X-rays passing through the table, relative to the horizontal direction view. Accordingly, the value of the projection onto the table 15 included in the raw data can be reduced, facilitating discrimination between the value of projection to the table 15 and the value of projection to the subject 11, and this allows setting of the table threshold lower than that of the second embodiment. Accordingly, with reducing the impact of the table 15, the ellipse 211 can be configured accurately in a size closer to the shape of the subject 11.

With reference to FIG. 5, there will be described an operation for creating the subject model 202 by the subject model generator 22 in the present embodiment. In the following, the description common to the second embodiment and the present embodiment will not be provided redundantly.

Figure 11A:
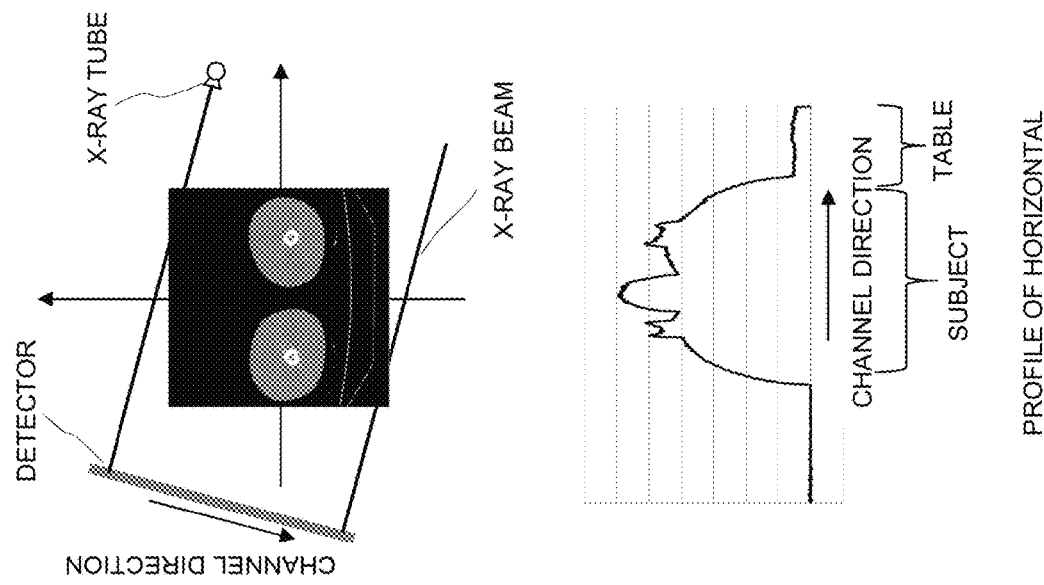
FIGS. 11A and 11B illustrate the imaging directions and data profiles of the raw data of a view inclined from the vertical direction and of a view inclined from the horizontal direction according to the fourth embodiment.
Figure 11B:
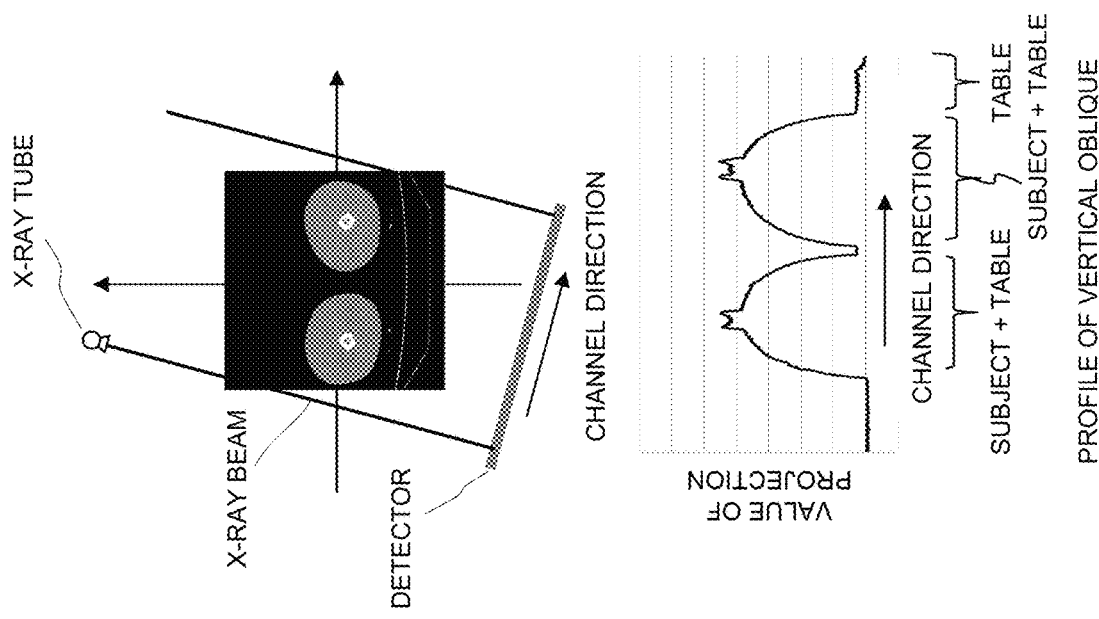

First, as shown in FIGS. 11A and 11B, the subject model generator 22 selects the vertical oblique view and the horizontal oblique view in step S5-1.

Let the inclination angle $\theta^v$[rad] denote the angle made by the vertical direction view and the vertical oblique view, and it is defined as $-\pi/4<\theta^v<\pi/4$ for distinguishing from the horizontal oblique view. Similarly, the inclination angle between the horizontal direction view and the horizontal oblique view is defined as $\theta^h$ ($-\pi/4<\theta^h<\pi/4$)[rad].

Next, in step S5-2, the subject model generator 22 creates, similar to the second embodiment, a profile in the channel direction, targeting profiles of the raw data of the vertical oblique view and the horizontal oblique view.

Furthermore, in step S5-3, similar to the second embodiment, the subject model generator 22 stores the channel number of the value of projection equal to or larger than the predetermined table threshold in the storage unit 33, thereby identifying a candidate of the subject. It should be noted that with respect to the vertical direction view and the horizontal direction view, the vertical oblique view and the horizontal oblique view have a lower value of projection of the table on the profile, relative to the horizontal direction view of the second embodiment, and the value of projection of the table 15 varies in response to the inclination angle of the view. Therefore, it is preferable that a plurality of table thresholds should be calculated or obtained by experiments in advance, in response to the inclination angle of the vertical oblique view or of the horizontal oblique view, and stored in the storage unit 33. The subject model generator 22 reads a value corresponding to the inclination angle selected in step S5-1 from the storage unit 33 and uses the value thus read out. Since the calculation of the channel number of the subject candidate is the same as the second embodiment, redundant description will not be provided.

Figure 12:
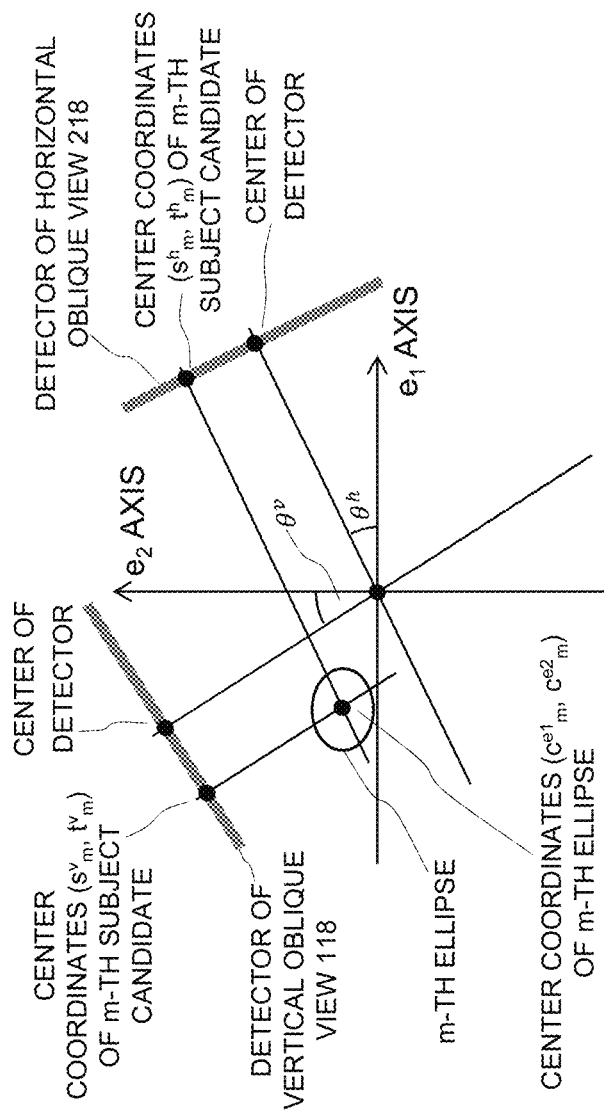
FIG. 12 illustrates a process of setting the ellipse based on the position and other information of the subject candidates obtained from the profile of the raw data according to the fourth embodiment.

Next, in step S5-4, the subject model generator 22 creates the ellipse 211 on the basis of the channel number of the subject candidate. Similar to the second embodiment, the subject model generator 22 calculates the coordinates of the center of the ellipse 211, for the m-th subject candidate of the profiles in the horizontal oblique view and in vertical oblique view. With reference to FIG. 12, this process will be described in the following. Similar to the second embodiment, the coordinate axes include axis $e_1$ indicating the horizontal direction, and axis $e_2$ indicating the vertical direction.

First as shown in FIG. 12, the subject model generator 22 calculates the coordinates $(s_m^v, t_m^v)$ of the central position of the m-th subject candidate projected to the detector 118 in the vertical oblique view, using the central position $c_m^v$ of the subject candidate on the detector 18 as given by Equation 1, the inclination angle $\theta^v$, and the distance from the rotation center to the detector 18.

Also for the horizontal oblique view, the subject model generator 22 calculates the coordinates $(s_m^h, t_m^h)$ of the central position of the m-th subject candidate projected to the detector 218 in the horizontal oblique view, using the central position $c_m^h$ of the subject candidate on the detector 18 as given by Equation 2, the inclination angle $\theta^h$, and the distance from the rotation center to the detector 18.

The center coordinates $(c_m^{e1}, c_m^{e2})$ of the m-th ellipse 211 takes the positional relationship with respect to the vertical oblique view and the horizontal oblique view as illustrated in FIG. 12. The subject model generator 22 obtains the line $e^2 = e^1 \tan\theta^v + t_m^v - s_m^v \tan\theta^v$, being parallel to the line connecting between the center of the detector 118 of the vertical oblique view and the rotation center, and passing through the coordinates $(s_m^v, t_m^v)$. Similarly, the subject model generator 22 obtains the line $e^2 = e^1 \tan\theta^h + t_m^h - s_m^h \tan\theta^h$, being parallel to the line connecting between the center of the detector 218 of the horizontal oblique view and the rotation center, and passing through the coordinates $(s_m^h, t_m^h)$. The subject model generator 22 obtains the point of intersection of the two lines, as the center coordinates of the ellipse, according to following Equations 13 and 14:

$$c_m^{e_1} = \frac{t_m^v - t_m^h + s_m^h \tan\theta^h - s_m^v \tan\theta^v}{(\tan\theta^h - \tan\theta^v)} \tag{13}$$

$$c_m^{e_2} = \frac{t_m^h \tan\theta^v - t_m^v \tan\theta^h + (s_m^v - s_m^h)\tan\theta^v \tan\theta^h}{\tan\theta^v - \tan\theta^h} \tag{14}$$

In addition, let "a" and "b" denote the major axis and the minor axis, respectively, of the m-th ellipse. The ellipse in this example is provided with the major axis and the minor axis, respectively agreeing with $e_1$ axis being the horizontal axis, and $e_2$ axis being the vertical axis. Any orientation may be selected for the major axis and the minor axis.

Figure 13:
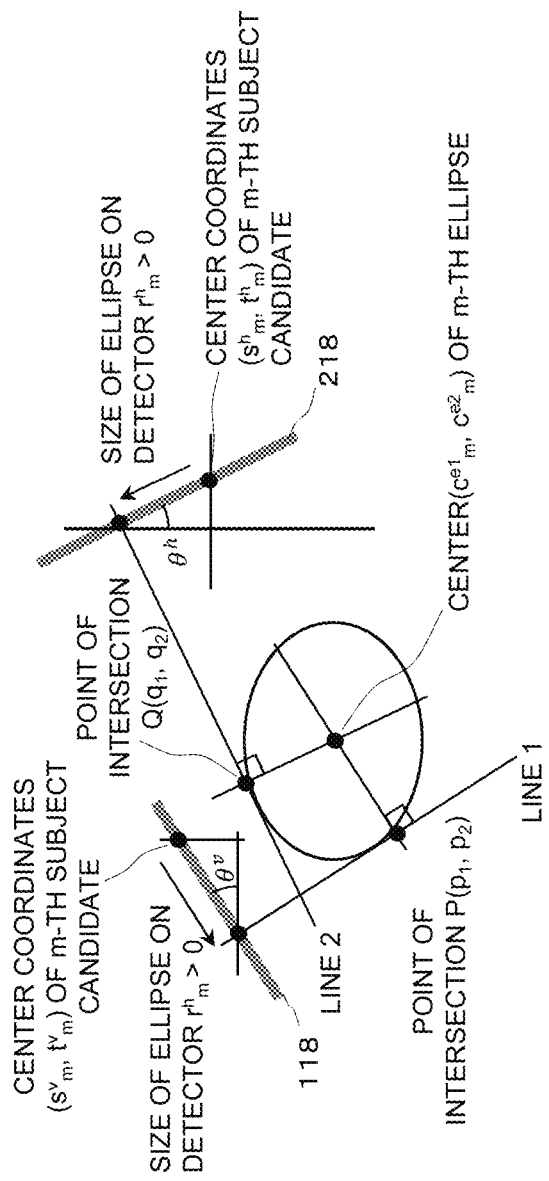
FIG. 13 illustrates the process of setting the ellipse based on the position and other information of the subject candidates obtained from the profile of the raw data according to the fourth embodiment.
Figure 14B:
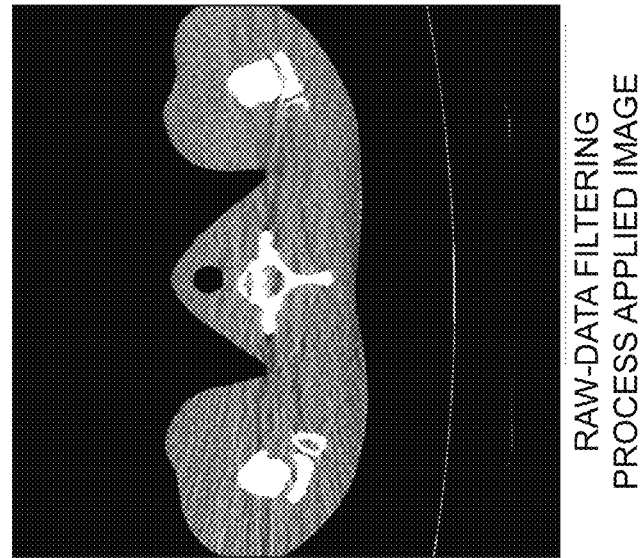
FIG. 14B shows an example of an image reconstructed from the raw data to which a smoothing filter was applied.
Figure 14A:
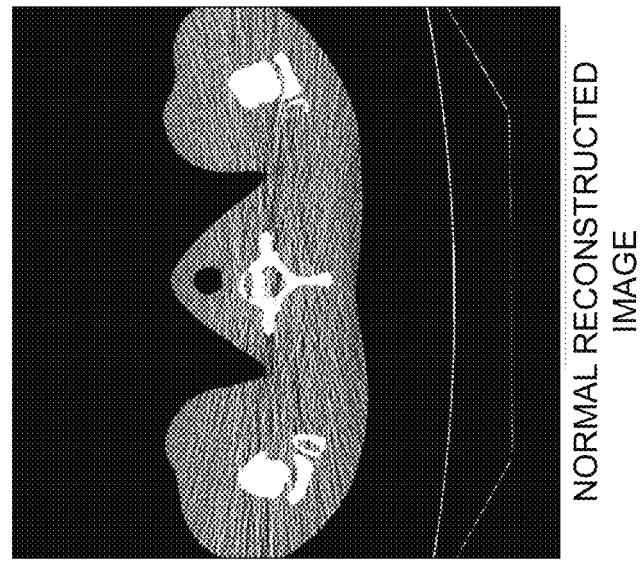
FIG. 14A shows an example of a normal reconstructed image of the X-ray CT system.

FIG. 13 is an enlarged view of the ellipse part shown in FIG. 12. First, the subject model generator 22 calculates according to Equation 3, the dimension of the ellipse $r_m^v$ on the detector 118 in the vertical oblique view. Similarly, the subject model generator 22 calculates according to Equation 4, the dimension of the ellipse $r_m^h$ the detector 218 in the horizontal oblique view.

Let line 1 denote the line passing through the point, $r_m^v$ away from the coordinates $(s_m^v, t_m^v)$ at the central position in the vertical oblique view on the detector 118, and intersecting the detector 118 at right angles. In addition, $P(p_1, p_2)$ denotes the point of intersection of the line drawn from the center of the ellipse 211, perpendicular to Line 1. Let line 2 denote the line passing through the point, $r_m^h$ away from the coordinates $(s_m^h, t_m^h)$ at the central position in the horizontal oblique view on the detector 218, and intersecting the detector 218 at right angles. In addition, $Q(q_1, q_2)$ denotes the point of intersection of the line drawn from the center of the ellipse 211, perpendicular to Line 2.

The ellipse that is inscribed on Line 1 and Line 2, with the center $(c_m^{e1}, c_m^{e2})$ is represented by $a^2 p_1^2 + b^2 p_2^2 = (p_1^2 + p_2^2)^2$, using the intersection point $P(p_1, p_2)$. Similarly, it is represented by $a^2 q_1^2 + b^2 q_2^2 = (q_1^2 + q_2^2)^2$, using the intersection point $Q(q_1, q_2)$. Therefore, "a" and "b" are eliminated from the equations above, and the following equations are derived:

$$a^2 = \frac{(p_1^2 + p_2^2)^2}{p_1^2} - \frac{p_2^2 q_1^2 (p_1^2 + p_2^2)^2 - p_1^2 p_2^2 (q_1^2 + q_2^2)^2}{p_1^2 (p_2^2 q_1^2 - p_1^2 q_2^2)} \tag{15}$$

$$b^2 = \frac{q_1^2 (p_1^2 + p_2^2)^2 - p_1^2 (q_1^2 + q_2^2)^2}{(p_2^2 q_1^2 - p_1^2 q_2^2)} \tag{16}$$

The subject model generator 22 calculates the coordinates of the intersection points $P(p_1, p_2)$ and $Q(q_1, q_2)$, based on the values $r_m^v, \theta^v, (s_m^v, t_m^v)$ and $r_m^h, \theta^h, (s_m^h, t_m^h)$, and determines the size (the major axis and the minor axis) of the ellipse by substituting the resultant values into Equations 15 and 16.

According to the configuration as described above, the ellipse 211 is provided by using the raw data of the views inclined with respect to the vertical view and the horizontal view, so as to create the subject model 202. The configuration and effects other than those described above are the same as the second embodiment, and redundant descriptions will not be given.

In the present embodiment, there has been described the configuration where the ellipse 211 is created from the raw data inclined in the vertical and horizontal directions. By combining the configuration of the present embodiment with the configuration where the ellipse 211 is created from the raw data of the vertical direction view or of the horizontal direction view as described in the second embodiment, an ellipse may be created on the basis of two views, for example, the vertical direction view and the horizontal oblique view. Then, in calculating the components of the subject model 202, i.e., total number, the positions, and the sizes of the ellipses 211, any combinations of views may be selected individually from the vertical direction view, the horizontal direction view, and the views inclined with respect to the vertical and horizontal directions.

Fifth Embodiment

In the present embodiment, when the ellipses of the subject model 202 are provided as described in the second embodiment, multiple subject candidates may be consolidated to reduce the number of ellipses 211. With this configuration, the subject model 202 can be created within a short amount of time, and thus computing of the sharpened image can be accelerated. In here, the description common to the second embodiment and the fourth embodiment will not be provided redundantly.

Figure 7B:
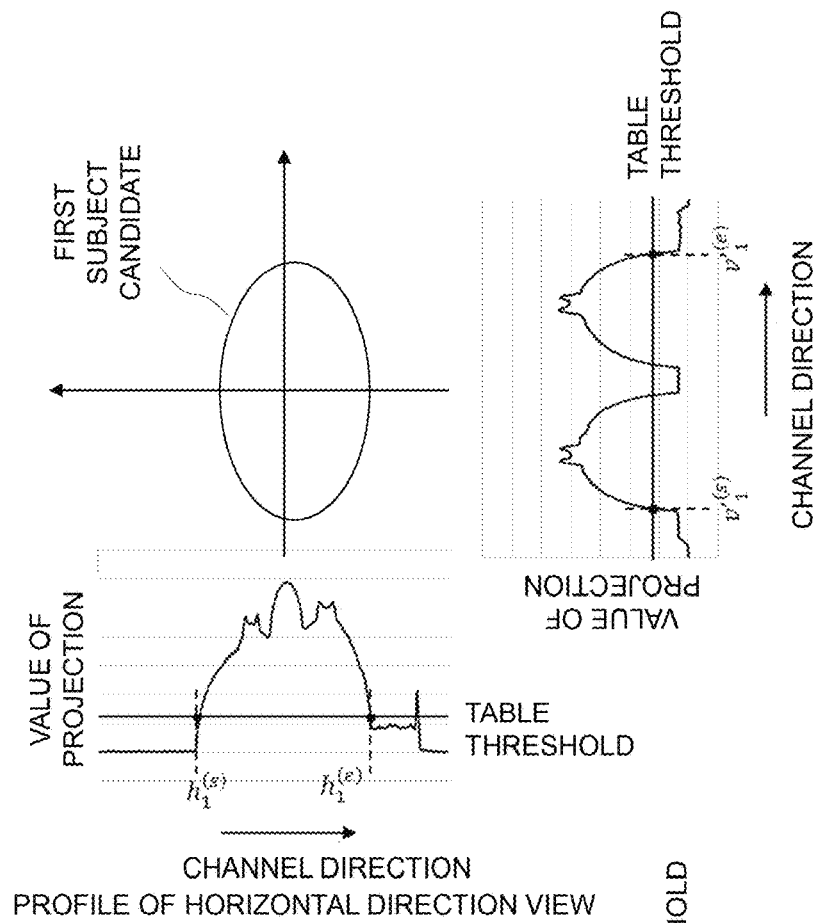
FIG. 7B illustrates a process for consolidating the subject candidates obtained from the profiles of the raw data and setting a reduced number of ellipses according to the fifth embodiment.
Figure 7A:
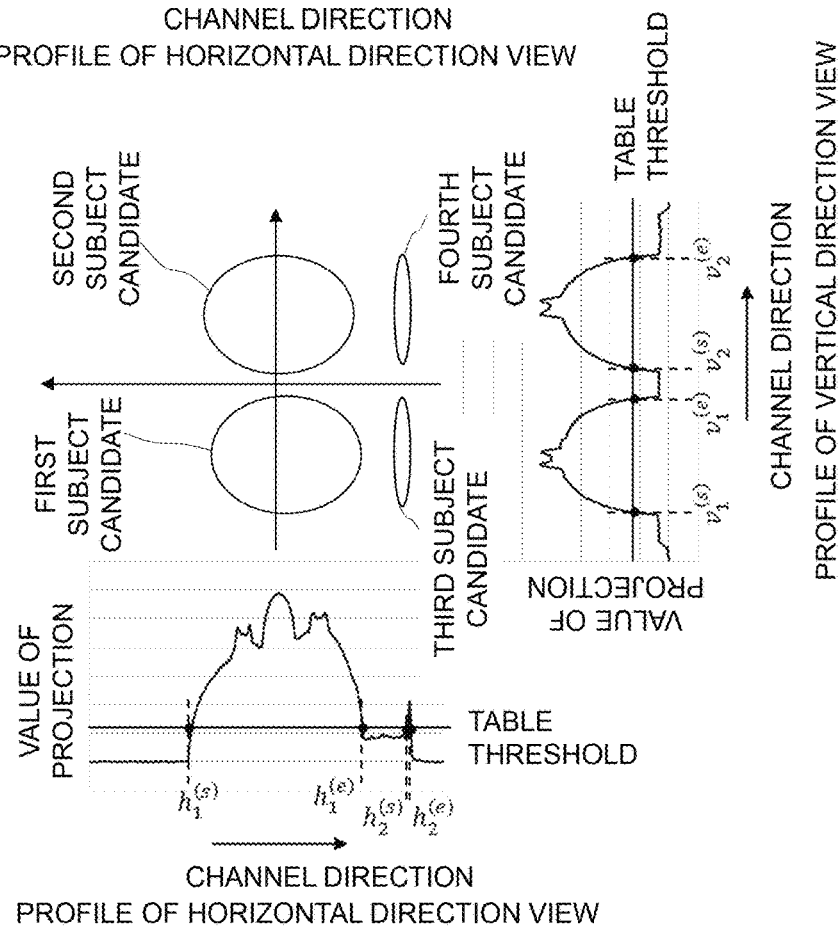
FIG. 7A illustrates a process of obtaining subject candidates from the profiles of the raw data and setting ellipses according to the second embodiment.

In order to compare the present embodiment with the second embodiment, taking the profile of FIG. 6 as an example, the conceptual diagrams of the process for identifying the subject 11 in step S5-3 are shown in FIGS. 7A and 7B, where the fifth embodiment is put in contrast with the second embodiment.

In the second embodiment, as shown in FIG. 7A, the subject candidate identified by the channel numbers $v_1^{(s)}$ and $v_1^{(e)}$ and the subject candidate identified by $v_2^{(s)}$ and $v_2^{(e)}$ are extracted from the profile of the vertical direction view. In addition, from the profile on the horizontal direction view, the subject candidate identified by $h_1^{(s)}$ and $h_1^{(e)}$ and the subject candidate identified by $h_2^{(s)}$ and $h_2^{(e)}$ are extracted. Therefore, the configuration of the second embodiment is to set the ellipses 211 associated with four subject candidates, based on the subject candidates identified by the two views.

FIG. 7B illustrates a conceptual diagram of the process for identifying the subject in the present embodiment. In the fifth embodiment, as a rule for the consolidation, there is provided an upper limit to the number of the subject candidates per profile (hereinafter, referred to as the upper-limit number of the candidates), and the subject model generator 22 consolidates the subject candidates, when the number of candidates exceeds the upper limit. The upper limit number of the candidates is defined in advance for each profile. FIG. 7B shows an example where the upper limit of the candidates of the vertical direction view is set to one. First, the subject model generator 22, according to the profile of the vertical direction view, consolidates the subject candidates identified by the channel numbers $v_1^{(s)}$ and $v_1^{(e)}$ with the subject candidate identified by $v_2^{(s)}$ and $v_2^{(e)}$, and then newly extracts the subject candidate identified by the channel numbers $v_1^{(s)}$ and $v_2^{(e)}$ in a manner that contains both subject candidates. In here, let $v'_1^{(s)}$ and $v'_1^{(e)}$ denote the channel numbers of the subject candidate after consolidation.

As the consolidation rule when the upper limit number of the candidates is larger than two, the subject model generator 22 repeats consolidation in ascending order from a smaller size of the subject candidate (smaller difference between the channel numbers) on the profile. In other words, the subject model generator 22 consolidates the smallest subject candidate among all the subject candidates, with another subject candidate that is next smaller out of all the subject candidates adjacent thereto, to create a new subject candidate. It should be noted if there is only one adjacent subject candidate, the consolidation is performed with this subject candidate. Next, the subject model generator 22 consolidates the smallest subject candidate among the subject candidates being unconsolidated and the post-consolidation subject candidate, with another subject candidate that is next smaller out of all the subject candidates adjacent thereto, thereby creating new subject candidate. The subject model generator 22 repeats this operation until the number of the subject candidates reaches the upper limit number thereof. Accordingly, small subject candidates are consolidated to reduce computation, along with maintaining estimated accuracy of a large subject candidate.

Similar to the second embodiment, the subject model generator 22 calculates the central position and the length of the ellipse of the consolidated subject candidate (ellipse 211), by using the channel numbers after the consolidation.

When the size of the subject candidate falls below a predetermined lower limit of the subject size (hereinafter, referred to as a lower-limit subject size), the subject model generator 22 may eliminate this subject candidate. For example, in the case of the horizontal direction view as shown in FIG. 7A, the subject candidates identified by the channel numbers $h_2^{(s)}$ and $h_2^{(e)}$ are excluded from the profile. In here, the subject model generator 22 obtains the size of the subject candidate, according to a difference between the two channel numbers $h_2^{(s)}$ and $h_2^{(e)}$. It is preferable to set the lower-limit subject size a value corresponding to 20 channels, for instance, in order to eliminate the part corresponding to the table, because a value of the raw data is prone to become higher due to the structure of the table. It is to be noted that lower-limit subject size may be determined to any value, on the basis of the balance between the detector element size per channel and the size of the subject.

Since exclusion of the subject candidates as described above changes the number of the subject candidates, it is desirable the subject model generator 22 should perform this exclusion process, prior to the aforementioned consolidation process.

In the present embodiment, a plurality of subject candidates on the profile can be consolidated into less number of subject candidates, as to both the vertical and horizontal direction views, to perform estimation.

Furthermore, the present embodiment may also be applied to the method for estimating the ellipse of the vertical or horizontal oblique view as described in the fourth embodiment.

DESCRIPTION OF SYMBOLS

1 . . . raw data acquisition part (scanner), 2 . . . arithmetic unit, 3 . . . I/O unit, 5 . . . operating unit, 11 . . . subject, 12 . . . X-ray generator, 13 . . . bow-tie filter, 14 . . . collimator, 15 . . . table, 17 . . . drive unit, 18 . . . X-ray detector, 19 . . . preamplifier, 20 . . . correction processor, 21 . . . image reconstructor, 22 . . . subject model generator, 23 . . . sharpening processor, 24 . . . image processor, 25 . . . image space model generator, 31 . . . display unit, 32 . . . input unit, 33 . . . storage unit, 40 . . . data collection system, 41 . . . A/D converter, 43 . . . central control unit, 45 . . . X-ray controller, 46 . . . high voltage generator, 47 . . . scanner controller, 48 . . . imaging space, 49 . . . region to be imaged, 50 . . . disc, 201 . . . smoothed image, 202 . . . subject model, 203 . . . image space model, 211 . . . predetermined shape, 221 . . . region of the peripheral part, 222 . . . region of the central part, 260 . . . structure, 118 . . . detector of vertical oblique view, 218 . . . detector of horizontal oblique view

What is claimed is:

1. An X-ray CT system comprising,
a raw data acquisition part configured to acquire raw data obtained by applying X-rays to a subject placed in imaging space and by detecting a distribution of X-ray strength passing through the subject, the raw data being associated with multiple views at different X-ray irradiation angles to the subject,
an image reconstructor configured to apply a smoothing process to the raw data associated with multiple views, followed by image reconstruction to obtain a smoothed image of a predetermined region to be imaged in the imaging space,
a sharpening processor configured to apply more intense sharpening to pixels in a region of a central part of the subject in the smoothed image, than to pixels in a region of a peripheral part of the subject, and
a subject model generator configured to create a subject model that represents a form and position of the subject in the region to be imaged, in an approximate manner, by using one or more predetermined shapes and the position thereof,
wherein the sharpening processor brings the subject model into correspondence with the smoothed image, and applies more intense sharpening to pixels in the region of the smoothed image corresponding to the region of the central part of the predetermined shape of the subject model, than to pixels in the region of the smoothed image corresponding to the region of the peripheral part of the predetermined shape.

2. The X-ray CT system according to claim 1, wherein, the subject model generator selects the raw data of one or more views from the raw data associated with multiple views, and creates the subject model on the basis of a distribution of signal strength of the raw data thus selected.

3. The X-ray CT system according to claim 1, wherein, the predetermined shape of the subject model is an ellipse.

4. The X-ray CT system according to claim 1, wherein, the sharpening processor increases a degree of sharpening gradually from the peripheral part to the central part of the predetermined shape of the subject model.

5. The X-ray CT system according to claim 4, wherein, when the subject model includes two or more predetermined shapes, the sharpening processor increases the degree of sharpening gradually from the peripheral part to the central part, as to each of the predetermined shapes.

6. The X-ray CT system according to claim 2, wherein, the subject model generator selects the raw data of two or more views, from the raw data associated with multiple views, and creates the subject model.

7. The X-ray CT system according to claim 6, wherein, the raw data of two or more views selected by the subject model generator includes a vertical direction view and a horizontal direction view.

8. The X-ray CT system according to claim 6, wherein, the raw data of two or more views selected by the subject model generator includes a view inclined at a certain angle relative to the vertical direction view and a view inclined at a certain angle relative to the horizontal direction view.

9. An X-ray CT system comprising:
a raw data acquisition part configured to acquire raw data obtained by applying X-rays to a subject placed in imaging space and by detecting a distribution of X-ray strength passing through the subject, the raw data being associated with multiple views at different X-ray irradiation angles to the subject,
an image reconstructor configured to apply a smoothing process to the raw data associated with multiple views, followed by image reconstruction to obtain a smoothed image of a predetermined region to be imaged in the imaging space,
a sharpening processor configured to apply more intense sharpening to pixels in a region of a central part of the subject in the smoothed image, than to pixels in a region of a peripheral part of the subject, and
a pixel-value variation calculator configured to obtain a degree of variation of pixel values between the pixels that are adjacent to each other in the smoothed image, wherein,
the sharpening processor reduces the rate of sharpening for the pixels with a high degree of variation in pixel value, relative to the pixels with a low degree of variation in pixel value.

10. The X-ray CT system according to claim 9, wherein, the pixel-value variation calculator creates an image space model representing a distribution of the degree of pixel-value variation between pixels adjacent to each other in the smoothed image, and
the sharpening processor varies the degree of sharpening in response to the distribution of the degree of pixel-value variation of the image space model.

11. The X-ray CT system according to claim 2, wherein, the subject model generator places the predetermined shape at a position corresponding to a range where the signal strength distribution of the selected raw data is equal to or larger than a predetermined threshold, and creates the subject model.

12. The X-ray CT system according to claim 11, wherein, the subject model generator reduces the number of the predetermined shapes, by consolidating the range where the signal strength distribution is equal to or larger than the predetermined threshold, so that the number of predetermined shapes is equal to or less than a predetermined upper limit.

* * * * *